US008067233B2

(12) United States Patent
Totey et al.

(10) Patent No.: US 8,067,233 B2
(45) Date of Patent: Nov. 29, 2011

(54) PLURIPOTENT EMBRYONIC-LIKE STEM CELLS DERIVED FROM CORNEAL LIMBUS, METHODS OF ISOLATION AND USES THEREOF

(75) Inventors: Satish Mahadeorao Totey, Wadala (IN); Subhadra Devi Kashyap, Navi (IN); Khan Firdos Alam, Navi (IN); Pai Rajarshi, Navi (IN); Khanna Aparna, Navi (IN); Tipnis Shabri, Bhandup (IN); Geeta Ravindran, Vikhroli (IN)

(73) Assignee: Reliance Life Science PVT. Ltd., Mumbia, Maharashtra (IN)

( * ) Notice: Subject to any disclaimer, the term of this patent is extended or adjusted under 35 U.S.C. 154(b) by 78 days.

(21) Appl. No.: 12/321,161

(22) Filed: Jan. 16, 2009

(65) Prior Publication Data
US 2009/0263878 A1  Oct. 22, 2009

Related U.S. Application Data

(63) Continuation of application No. 11/063,335, filed on Feb. 22, 2005, now abandoned.

(60) Provisional application No. 60/621,476, filed on Oct. 22, 2004.

(51) Int. Cl.
*C12N 5/00* (2006.01)
(52) U.S. Cl. ........ 435/325; 435/363; 435/366; 435/374; 435/383; 435/384
(58) Field of Classification Search .................. None
See application file for complete search history.

(56) References Cited

U.S. PATENT DOCUMENTS

| | | | |
|---|---|---|---|
| 5,411,883 A * | 5/1995 | Boss et al. ............... | 435/29 |
| 6,152,142 A | 11/2000 | Tseng | |
| 6,200,806 B1 | 3/2001 | Thomson | |
| 6,610,538 B2 | 8/2003 | DeLuca et al. | |
| 6,921,665 B2 | 7/2005 | McWhir et al. | |
| 2002/0039788 A1 | 4/2002 | Isseroff et al. | |
| 2003/0161817 A1 | 8/2003 | Young et al. | |
| 2003/0186439 A1 | 10/2003 | Nakauchi et al. | |
| 2003/0208266 A1 | 11/2003 | Tsai | |
| 2003/0235563 A1 | 12/2003 | Strom et al. | |
| 2004/0018617 A1 * | 1/2004 | Hwang ..................... | 435/354 |
| 2004/0033214 A1 | 2/2004 | Young et al. | |
| 2005/0136536 A1 | 6/2005 | Anderson et al. | |

FOREIGN PATENT DOCUMENTS

| | | |
|---|---|---|
| EP | 0572364 A2 | 12/1993 |
| EP | 0572364 A3 | 12/1993 |
| WO | WO 00/73421 A2 | 12/2000 |
| WO | WO 00/73421 A3 | 12/2000 |
| WO | WO 03/030959 A1 | 4/2003 |
| WO | WO 03/093457 A1 | 11/2003 |

OTHER PUBLICATIONS

Zhao et al. Dev Biol 2002;250:317-31.*
Watanabe et al. FEBS Let 2004;565:6-10.*
Moreadith et al., J. Mol. .Med., 1997.*
Pera et al. Journal of Cell Science 113: 5-10 (2000).*
Theise, Stem cell Reviews 2005;1:9-13.*
Pincock, The Scientist. Feb. 26, 2007.*
Serafini and Verfaillie, Semi Reprod Med 2006;24:379-88.*
Aldhous, New Scientist. Feb. 15, 2007;2591:12.*
Geraerts et al. Adv Biochem Eng Biotechnol 2009;114:1-21.*
Potten, *Stem Cells in Gastrointestinal Epithelium: Numbers, Characteristics and Death*, Phil. Trans. R. Soc. Lond. B., 353:821-830, 1998.
Prusa, et al., *Oct-4-Expressing Cells in Human Amniotic Fluid: a New Source for Stem Cell Research?*, Hum. Reprod., 18(7)1489-1493, 2003.
Reubinoff, et al., *Embryonic Stem Cell Lines from Human Blastocysts: Somatic Differentiation* in vitro, Nature Biotech., 18:399-403, 2000.
Schermer, et al., *Differentiation-related Expression of a Major 64K Corneal Keratin* in Vivo *and in Culture Suggests Limbal Location of Corneal Epithelial Stem Cells*, J. Cell Biol., 103:49-62, 1986.
Seigel, et al., *Human Corneal Stem Cells Display Functional Neuronal Properties*, Mol. Vis., 9:159-63, 2003.
Spier, *Large-scale Mammalian Cell Culture: Methods, Applications and Products*, Curr. Opin. Biotechnol., 2:375-79, 1991.
Thomson, et al., *Embryonic Stem Cell Lines Derived from Human Blastocysts*, Science, 282:1145-1147, 1998.
Toma, et al., *Isolation of Multipotent Adult Stem Cells from the Dermis of Mammalian* Skin, Nat. Cell. Biol., 3:778-84, 2001.
Tsai, et al., *Reconstruction of Damaged Corneas by Transplantation of Autologous Limbal Epithelial Cells*, N. Engl. J. Med., 343(2)86-93, 2000.
Tseng, *Regulation and Clinical Implications of Corneal Epithelial Stem Cells*, Mol. Biol. Rep., 23:47-58, 1996.
Tseng, et al., *Amniotic Membrane Transplantation With or Without Limbal Allografts for Corneal Surface Reconstruction in Patients with Limbal Stem Cell Deficiency*, Arch. Ophthalmol., 116:431-41, 1998.
Watt, *Epidermal Stem Cells: Markers, Patterning and the Control of Stem Cell F*ate, Phil. Trans. R. Soc. Lond. B., 353:831-837, 1998.
Weissman, *Translating Stem and Progenitor Cell Biology to the Clinic: Barriers and Opportunities*, Science, 287:1442-1446, 2000.
Wells, et al., *Cytokeratin 18 is Expressed on the Hepatocyte Plasma Membrane Surface and Interacts with Thrombin-Antithrombin Complexes*, J. Biol. Chem., 272(45)28574-28581, 1997.
Xu, et al., *Feeder-free Growth of Undifferentiated Human Embryonic Stem Cells*, Nat. Biotechnol, 19:971-4, 2001.
Young, et al., *Clonogenic Analysis Reveals Reserve Stem Cells in Postnatal Mammals. II. Pluripotent Epiblastic-Like Stem Cells*, Anat. Rec., 277A(1):178-203, 2004.

(Continued)

*Primary Examiner* — Q. Janice Li
(74) *Attorney, Agent, or Firm* — Vinson & Elkins LLP

(57) ABSTRACT

The present disclosure describes mammalian pluripotent embryonic-like stem cells (ELSCs) isolated from corneal limbal tissue, a non-embryonic tissue. The ELSCs of the present disclosure are capable of proliferating in an in vitro culture, maintain the potential to differentiate into cells of endoderm, mesoderm, and ectoderm lineage in culture, and are capable of forming embryoid-like bodies when placed in suspension culture. Thus, these cells possess multi-lineage differentiation potential and self-renewing capability. ELSCs may be a promising therapeutic tool, and may provide new therapeutic alternatives for various diseases, conditions, and injuries.

16 Claims, 9 Drawing Sheets

OTHER PUBLICATIONS

Anderson, et al., "Amniotic Membrane Transplantation for Partial Limbal Stem Cell Deficiency", Br. J. Opthalmol. 85:567-575, 2001.

Andrews, et al., "Embryonic Stem (ES) Cells and Embryonal Carcinoma (EC) Cells: Opposite Sides of the Same Coin", Biochem. Soc. Trans. 33:1526-1530, 2005.

Ausubel, et al., "Techniques for Mammalian Cell Tissue Culture", Current Protocols in Molecular Biology, 4:Appendix 3F, pp. A.3F.1-A.3F.10, 1994.

Deschambeault, et al., "In vitro Characterization of Human Limbal Epithelial Cells Isolated From the Four Quandrants", ARVO Annual Meeting Abstract Search and Program Planner, vol. 2003, Abstract No. 1357, 2003.

Du, et al., "Functional Reconstruction of Rabbit Corneal Epithelium by Human Limbal Cells Cultured on Amniotic Membrane", Mol. Vis. 9:635-643, 2003.

Dua, et al., "Limbal Stem Cells of the Corneal Epithelium", Surv. Ophthalmol. 44:415-425, 2000.

Grueterich, et al., "Connexin 43 Expression and Proliferation of Human Limbal Epithelium on Intact and Denuded Amniotic Membrane", Invest. Ophthalmol. Vis. Sci. 43:63-71, 2002.

Holland, et al., "Epithelial Transplantation for the Management of Severe Ocular Surface Disease", Trans. Am. Ophthalmol. Soc. 94:677-743, 1996.

Koestenbauer, et al., "Embryonic Stem Cells: Similarities and Differences Between Human and Murine Embryonic Stem Cells", Am. J. Reprod. Immunol. 55:169-180, 2006.

Koizumi, et al., "Amniotic Membrane as a Substrate for Cultivating Limbal Corneal Epithelial Cells for Autologous Transplantation in Rabbits", Cornea 19:65-71, 2000.

Koizumi, et al., "Cultivated Corneal Epithelial Stem Cell Transplantation in Ocular Surface Disorders", Ophthalmology 108:1569-1574, 2001.

Koizumi, et al., "Cultivation of Corneal Epithelial Cells on Intact and Denuded Human Amniotic Membrane", Invest. Ophthalmol. Vis. Sci. 41:2506-2513, 2000.

Lindstrom, "Advances in Corneal Transplantation", N. Engl. J. Med. 315:57-59, 1986.

McCloskey, et al., "Magnetophoretic Cell Sorting is a Function of Antibody Binding Capacity", Biotechnol. Prog. 19:899-907, 2003.

Odorico, et al., "Multilineage Differentiation from Human Embryonic Stem Cell Lines", Stem Cells 19:193-204, 2001.

PCT/IB2005/00203, International Search Report, Feb. 28, 2007.

Pellegrini, et al., "Long-term Restoration of Damaged Corneal Surfaces with Autologous Cultivated Corneal Epithelium", Lancet 349:990-993, 1997.

Prabhasawat, et al., "Impression Cytology Study of Epithelial Phenotype of Ocular Surface Reconstructed by Preserved Human Amniotic Membrane", Arch. Ophthalmol. 115:1360-1367, 1997.

Shimazaki, et al., "Amniotic Membrane Transplantation for Ocular Surface Reconstruction in Patients with Chemical and Thermal Burns", Ophthalmology 104:2068-2076, 1997.

Shimazaki, et al., "Transplantation of Human Limbal Epithelium Cultivated on Amniotic Membrane for the Treatment of Severe Ocular Surface Disorders", Ophthalmology 109:1285-1290, 2002.

Tan, et al., "Limbal Transplantation", Ophthalmology 103:29-36, 1996.

Tsai, et al., "Comparison of Limbal and Conjunctival Autograft Transplantation in Corneal Surface Reconstruction in Rabbits", Ophthalmology 97:446-455, 1990.

Tseng, et al., "Amniotic Membrane Transplantation for Conjunctival Surface Reconstruction", Am. J. Ophthalmol. 124:765-774, 1997.

Ulloa-Montoya, et al., "Culture Systems for Pluripotent Stem Cells", J. Biosci. Bioeng. 100:12-27, 2005.

Xiong, et al., Culture Above Feeder 3T3 Cells in Serum-complemented, Reduced [Ca2+] Medium Allows Generation of Undifferentiated Confluent Monolayers of Limbal Epithelial Cells, Invest. Ophthalmol. Vis. Sci. 40: S324 (Abstract 1718-B626), 1999.

U.S. Appl. No. 11/043,019, Office Action mailed Aug. 9, 2006.

U.S. Appl. No. 11/043,019, Response filed Nov. 10, 2006 to Office Action mailed Aug. 9, 2006.

U.S. Appl. No. 11/043,019, Office Action mailed Jan. 31, 2007.

U.S. Appl. No. 11/043,019, Response field Apr. 30, 2007 to Office Action mailed Aug. 9, 2006.

U.S. Appl. No. 11/043,019, Office Communication mailed Jun. 6, 2007.

U.S. Appl. No. 11/043,019, Office Action mailed Aug. 24, 2007.

U.S. Appl. No. 11/043,019, Response filed Jan. 24, 2008 to Office Action mailed Aug. 24, 2007.

U.S. Appl. No. 11/043,019, Office Action mailed Apr. 15, 2008.

Abeyta, et al., *Unique Gene Expression Signatures of Independently-derived Human Embryonic Stem Cell Lines*, Hum. Mol. Genet., 13:6:601-608, 2004.

Alison and Sarraf, *Hepatic Stem Cells*, J. of Hepatol., 29:676-682, 1998.

Cotsarelis, et al., *Existence of Slow-Cycling Limbal Epithelial Basal Cells that can be Preferentially Stimulated to Proliferate: Implications on Epithelial Stem Cells*, Cell, 57:201-209, 1989.

Furusawa, et al., *Embryonic Stem Cells Expressing Both Platelet Endothelial Cell Adhesion Molecule-1 and State-Specific Embryonic Antigen-1 Differentiate Predominantly into Epiblast Cells in a Chimeric Embryo*, Biol. of Reprod., 70:1452-1457, 2004.

Gage, F.H., *Mammalian Neural Stem Cells*, Science, 287:1433-1438, 2000.

Gearhart, J., *New Potential for Human Embryonic Stem Cells*, Science, 282:1061-62, 1998.

Henderson, et al., *The Long Term Outcome of Limbal Allowgrafts: The Search for Surviving Cells*, Br. J. Opthalmol., 85:604-609, 2001.

Howell, et al., *Pluripotent Stem Cells Identified in Multiple Murine Tissues*, Ann. N.Y. Acad. Sci.,996:158-173, 2003.

Hu and Aunins, *Large-scale Mammalian Cell Culture*, Curr. Opin. Biotechnol., 8:148-153, 1997.

Jiang, et al., *Pluripotency of Mesemchymal Stem Cells Derived from Adult Marrow*, Nature, 418:41-48, 2002.

Li, et al., *Pluripotent Stem Cells from the Adult Mouse Inner Ear*, Nature Med., 9(10)1293-1299, 2003.

Moore, et al., *The Corneal Epithelial Stem Cell*, DNA and Cell Biol., 21(5/6)443-51, 2002.

Pellegrini, et al., *p63 Identifies Keratinocyte Stem Cells*, Proc. Natl. Acad. Sci. USA, 98(6)3156-61, Mar. 2001.

Pittenger, et al.,*Multilineage Potential of Adult Human Mesenchymal Stem Cells*, Science, 284:143-147, 1999.

\* cited by examiner

PLURIPOTENT EMBRYONIC-LIKE STEM CELLS DERIVED FROM CORNEAL LIMBUS, METHODS OF ISOLATION AND USES THEREOF

STATEMENT REGARDING FEDERALLY SPONSORED RESEARCH OR DEVELOPMENT

Not applicable.

BACKGROUND OF THE INVENTION

1. Field of the Invention

The present disclosure relates to purified preparations of mammalian pluripotent stem cells, preferably human pluripotent stem cells, derived from corneal limbus tissue. In preferred embodiments, the pluripotent limbal stem cell lines are self-renewing and have the ability to differentiate into tissues derived from all three embryonic germ layers (endoderm, mesoderm and ectoderm). Methods for isolating pluripotent limbal stem cell lines and methods of their use are also disclosed.

2. Description of Related Art

In early development, the ultimate source of all tissues in a mammalian embryo or fetus are stem cells. In the embryonic stage embryonic stem cells (ES cells) are totipotent and therefore capable of developing into all the cells of a complete organism. Cellular development occurs through several phases, including cellular proliferation, lineage commitment, and lineage progression, resulting in the formation of differentiated cell types. There are three main lineages that are derived from embryonic germ layers: ectoderm, mesoderm and endoderm. The ectoderm germ layer forms the epidermis of the skin, sense organs, nervous system, and spinal cord. The mesoderm germ layer forms smooth muscle, connective tissues, blood vessels, heart, blood cells and bone marrow, reproductive organ, excretory system, striated muscles, and skeletal muscles. Finally, the endoderm germ layer forms epithelial linings of respiratory and gastrointestinal tract, pharynx, esophagus, stomach, intestine, and other associated organs. ES cells are referred to as pluripotent stem cells because they can differentiate into almost all cell types in an adult organism.

During the last decade there has been ongoing research on the isolation and use of ES cells and cell lines, which in addition to having the ability to develop into most of the specialized cells in the human body also have the capacity to divide and proliferate indefinitely in culture. ES cells are often referred to as pluripotent stem cells because they are not fixed in their developmental potentialities and can differentiate into many different cell types in vitro. Cultured ES cells that are highly pluripotent can form clumps of cells in suspension culture referred to as embryoid bodies. ES cells were isolated from humans relatively recently (Thomson et al., (1998) Science 282:1145-1147; Gearhart, (1998) Science 282:1061-62). In embryoid bodies derived from human ES cells it is possible to discern differentiated cells bearing markers of a wide variety of cell types.

The isolation of human ES cells offers the promise of a remarkable array of novel therapeutics. Biologic therapies derived from such cells through tissue regeneration and repairs, as well as through targeted delivery of genetic material, are expected to be effective in the treatment of a wide range of medical conditions. However, despite the enormous potential of these materials, serious ethical issues related to the use of human pluripotent stem cells derived from human embryos or from fetal tissue obtained from terminated pregnancies make stem cell research and treatments problematic. In addition, technical issues associated with the use of ES cells are problematic. Tissues or cells derived from ES cells are not ideal for use in medical treatments because generally the ES cells will not be derived from the patient who will ultimately be receiving the treatment. Use of autologous tissues is preferred for stem-cell-based therapies in order to avoid tissue rejection problems.

I. Adult Stem Cells

The problems associated with human ES cells led many researchers to turn their attention to adult tissues as a possible source of undifferentiated stem cells with properties similar to those of ES cells or germ cells derived from fetal tissue. It was known that after birth and throughout adulthood a small number of specialized stem cells are retained in an organism for the replacement of cells and the regeneration of tissues. Indeed, adult stem cells (also referred to as "tissue-specific stem cells") have been found in very small numbers in various tissues of the adult body, including bone marrow, (Weissman, (2000) Science 287:1442-1446), neural tissue (Gage, (2000) Science 287:1433-1438), gastrointestinal tissue (Potten, (1998) Phil. Trans. R. Soc. Lond. B. 353:821-830), epidermal tissue (Watt, (1997) Phil. Trans. R. Soc. Lond. B. 353:831), hepatic tissue (Alison and Sarraf, (1998) J. Hepatol. 29:678-683), and mesenchymal tissue. (Pittenger et al., (1999) Science 284:143-147).

Nevertheless, while some potential sources of adult stem cells have been identified, to date adult stem cells have not been found to be an adequate replacement for ES cells. First, adult stem cells can be difficult to isolate because they are usually present only in minute quantities in tissues that are often not easily accessible, and their numbers appear to decrease with age. Second, adult stem cells appear to be a less desirable source of cultured tissue than ES cells because they have a shorter life span and less capacity for self-renewal. Third, adult stem cells are believed to be tissue specific and not pluripotent, generally capable of giving rise only to new cells of a few types closely related to their tissue of origin.

One particularly notable difference between ES cells and adult stem cells is that ES cells in suspension culture are capable of forming aggregates of cells known as embryoid bodies. These embryoid bodies usually contain germ cells of all three lineages that differentiate into various lineage-committed tissues. Therefore, embryoid bodies can be useful in the preparation of different types of differentiated cells in culture. To date, no other isolated adult stem cell lines have been reported that are capable of forming structures similar to embryoid-like bodies in culture.

Recently, however, it has been suggested that some adult stem cells have the capacity to be pluripotent. The most fully characterized are the hematopoetic stem cells known as bone marrow stromal cells or mesenchymal stem cells (Jiang et al., (2002) Nature 418:41-48). These were the first adult stem cells found to have pluripotent properties. Pluripotent adult stem cells have also been isolated from liver (U.S. Publ. No. 2003/0186439), mouse inner ear (Li and Heller, (2003) Nat. Med. 9:1293-1299), and amniotic fluid (Prusa et al., (2003) Hum. Reprod. 18:1489-1493). Pluripotent adult stem cells have also been recently described in many tissues such as skeletal muscle, brain, and intestinal epithelium (Howell et al., (2003) Ann. N.Y. Acad. Sci. 996:158-173). Still, while these papers report isolated or identified adult stem cells that are pluripotent, these "pluripotent" adult stem cells, unlike ES cells, differentiate into only a few lineages. In addition, none of the isolated adult stem cells reported to date appear to be capable of forming embryoid-like bodies in culture in a manner similar to ES cells.

II. Corneoscleral Limbus

Similar to the other sources of adult stem cells referenced above, it is known that adult stem cells are present in the corneoscleral limbus of the eye. These cells participate in the dynamic equilibrium of the corneal surface and replace superficial epithelial cells that are shed and sloughed off during eye-blinking. Severe damage to the limbal stem cells from chemical or thermal burns, contact lenses, severe microbial infection, multiple surgical procedures, cryotherapy, or diseases such as Steven-Johnson syndrome or ocular cicatrical pemphigoid can lead to destruction of limbal stem cells and limbal stem cell deficiency which can lead to an abnormal corneal surface, photophobia, and reduced vision (Anderson et al., (2001) Br. J. Opthalmol. 85:567-575). This damage cannot be repaired without the re-introduction of a source of limbal stem cells (Tseng et al., (1998) Arch. Opthalmol. 116: 431-41; Tsai et al., (2000) N. Engl. J. Med. 343:86-93; Henderson et al., (2001) Br. J. Opthalmol. 85:604-609). Thus limbal stem cells, with their high proliferative capacity, are clearly crucial for the maintenance of a viable ocular surface because they provide an unbroken supply of corneal epithelial cells necessary to maintain the equilibrium of the corneal surface (Tseng, (1996) Mol. Biol. Rep. 23:47-58).

Experiments conducted in the 1980s first indicated the existence of limbal cells in the corneal epithelium (Schermer et al., (1986) J. Cell Biol. 103:49-62; Cotsarelis et al., (1989) Cell 57:201-209). Although it was later suggested that the transcription factor P-63 was a specific marker for human corneal stem cells, this marker is also expressed in other epithelial cells such as skin, and therefore is not specific to corneal stem cells. In addition, although P-63 expression has been shown to be principally limited to the basal limbal region in human corneas (Moore et al., (2002) DNA Cell Biol. 21:443-51), in mice expression of this transcription factor was maximal in paracentral cornea tissue rather than limbus (Moore et al., (2002) DNA Cell Biol. 21:443-451). Therefore, currently there is no known definitive stem cell marker for limbal epithelial stem cells.

It would be desirable to identify a source of adult stem cells that are capable of self-renewal in culture and that are pluripotent and ES cell-like in their ability to differentiate into cells of all three major lineages: ectoderm, mesoderm and endoderm. Further, it would be desirable to isolate and culture these adult stem cells, and to induce them to differentiate into various cell types.

BRIEF SUMMARY OF THE INVENTION

The present disclosure describes the isolation of mammalian pluripotent embryonic-like stem cells (ELSCs) derived from non-embryonic tissue, preferably corneal limbal tissue. In particular, the present disclosure provides isolated mammalian pluripotent ELSCs which:

(i) are capable of proliferating in an in vitro culture,
(ii) maintain the potential to differentiate into cells of endoderm, mesoderm, and ectoderm lineage in culture, and
(iii) are capable of forming embryoid-like bodies when placed in suspension culture.

In preferred embodiments the isolated ELSCs are human ELSCs. In related preferred embodiments, the ELSCs are derived from corneoscleral limbus tissue, preferably human tissue. In other preferred embodiments, the isolated ELSCs remain substantially undifferentiated in an in vitro culture for at least about 20 passages, more preferably at least about 50 passages, and most preferably at least about 100 passages in culture. Preferably, after multiple passages in culture the substantially undifferentiated ELSCs maintain normal karyotype and high telomerase activity. In further embodiments, the isolated ELSCs have the potential to terminally differentiate into cells or tissues of endoderm, mesoderm, or ectoderm lineage.

The present disclosure also provides isolated mammalian pluripotent ELSCs which:

(i) are isolated from corneoscleral limbus,
(ii) are capable of proliferating in an in vitro culture, and
(iii) maintain the potential to differentiate into lineage-committed endodermal, ectodermal, or mesodermal cells.

In preferred embodiments the isolated ELSCs are human ELSCs, which are more preferably SSEA-4 positive. In related embodiments, the corneoscleral limbus is isolated from a human subject. Preferably, the isolated ELSCs are capable of forming embryoid-like bodies when placed in suspension culture. In other preferred embodiments, the isolated ELSCs remain substantially undifferentiated in an in vitro culture for at least about 20 passages, more preferably at least about 50 passages, and most preferably at least about 100 passages in culture. Preferably, after multiple passages in culture the substantially undifferentiated ELSCs maintain normal karyotype and high telomerase activity. In further embodiments, the isolated ELSCs have the potential to terminally differentiate into cells or tissues of endoderm, mesoderm, or ectoderm lineage.

The present disclosure also provides methods of isolating a population of mammalian pluripotent embryonic-like stem cells (ELSCs), comprising the steps of:

(a) isolating corneal limbal tissue from a donor;
(b) culturing the corneal limbal tissue to expand corneal limbal cells in culture; and
(c) isolating a population of pluripotent ELSCs from the cultured corneal limbal cells by sorting the corneal limbal cells to select for one or more undifferentiated cell-specific surface markers.

In preferred embodiments the isolated population of pluripotent ELSCs are human ELSCs, which are more preferably SSEA-4 positive. In other embodiments, the donor of the corneal limbal tissue is human. In certain embodiments, the corneal limbal tissue is cultured in culture media such as DMEM or F12, further supplemented with a nutrient serum and one or more soluble factors selected from the group consisting of dimethyl sulphoxide (DMSO), recombinant human epidermal growth factor (rhEGF), insulin, sodium selenite, transferrin, basic fibroblast growth factor (bFGF), and leukemia inhibitory factor (LIF). Preferably, the corneal limbal tissue is cultured until the corneal limbal cells in the culture become confluent. In certain embodiments, the corneal limbal tissue is cultured on an extracellular matrix, for example Matrigel™, laminin, collagen-IV, poly-L-lysine, gelatin, poly-L-ornithin, fibronectin, and combinations thereof, or mammalian amniotic membrane. When the corneal limbal tissue is cultured on an extracellular matrix, the above methods preferably further comprise the step of dissociating the cultured corneal limbal cells from the extracellular matrix prior to isolating the pluripotent ELSCs.

In preferred embodiments, the corneal limbal cells are sorted using methods well known to those of skill in the art, for example magnetic-affinity cell sorting (MACS) or fluorescence-activated cell sorting (FACS) to isolate a population of pluripotent ELSCs. In other embodiments, the one or more undifferentiated cell-specific markers selected for to isolate pluripotent ELSCs include but are not limited to SSEA-4, SSEA-3, CD73, CD105, CD31, CD54, and CD117. In preferred embodiments, corneal limbal cells are sorted to select for SSEA-4 positive ELSCs. In certain embodiments, the sorted ELSCs comprise at least about 80%, 90%, 95%, 98%, or 99% pluripotent ELSCs that are SSEA-4 positive. In preferred embodiments, the isolated population of pluripotent ELSCs comprise at least about 70%, 80%, 90%, 95%, 98%, or 99% pluripotent ELSCs. Preferably the isolated population of pluripotent ELSCs are further cultured to produce an embryonic-like stem cell line. In certain embodiments, the pluripotent ELSCs are cultured in culture media such as DMEM or F12, further supplemented with a nutrient serum and one or more soluble factors selected from the group consisting of DMSO, rhEGF, insulin, sodium selenite, transferrin, bFGF, and LIF.

In alternate embodiments, pluripotent ELSCs isolated by the methods disclosed herein are capable of proliferating and maintaining the potential to differentiate in vitro or in vivo into cells or tissues of endoderm, mesoderm or endoderm lineage. Preferably, the isolated pluripotent ELSCs are also capable of forming embryoid-like bodies, for example when placed in suspension culture. In other preferred embodiments, the isolated ELSCs remain substantially undifferentiated in an in vitro culture for at least about 20 passages, more preferably at least about 50 passages, and most preferably at least about 100 passages in culture. Preferably, after multiple passages in culture the substantially undifferentiated ELSCs maintain normal karyotype and high telomerase activity. In further embodiments, the isolated ELSCs have the potential to terminally differentiate into cells or tissues of endoderm, mesoderm, or ectoderm lineage.

In further embodiments the isolated pluripotent ELSCs, preferably human ELSCs, are further differentiated in culture into endodermal lineage-committed cells or tissues, mesodermal lineage-committed cells or tissues, or ectodermal lineage-committed cells or tissues. Alternatively, the isolated pluripotent ELSCs are further differentiated into endodermal lineage-committed cells or tissues, mesodermal lineage-committed cells or tissues, or ectodermal lineage-committed cells or tissues in vivo. In other embodiments, these ELSCs are further differentiated by exposing the ELSCs to one or more agents known to induce differentiation of pluripotent embryonic stem (ES) cells, including but not limited to acidic fibroblast growth factor, bFGF, platelet-derived growth factor (PDGF), insulin, retinoic acid, transferrin, insulin-transferrin-selenious acid (ITS), dexamethasone, sodium butyrate, DMSO, nerve growth factor (NGF), Cytosine beta-d-Arabino Furanoside (Ara C), glial cell line-derived neurotrophic factor gene (GDNF), transforming growth factor β3 (TGF-β3), ascorbic acid, N-acetyl Cysteine, dibutaryl cyclic AMP, Neurturin, transforming growth factor β1 (TGF-β1), insulin-like growth factor I or II (IGF-I or IGF-II), epidermal growth factor (EGF), bone morphogenic proteins 2 (BMP-2), β glycerophosphate, ascorbic acid 2 phosphate, 5-Aza-deoxy-cytidine, oncostatin, hepatocyte growth factor (HGF), progesterone, nicotinamide, or any combination thereof.

BRIEF DESCRIPTION OF THE SEVERAL VIEWS OF THE DRAWINGS

The following drawings form part of the present specification and are included to further demonstrate certain aspects of the present disclosure. The present disclosure may be better understood by reference to one or more of these drawings in combination with the detailed description of specific embodiments presented herein.

DETAILED DESCRIPTION OF THE INVENTION

Figure 1:
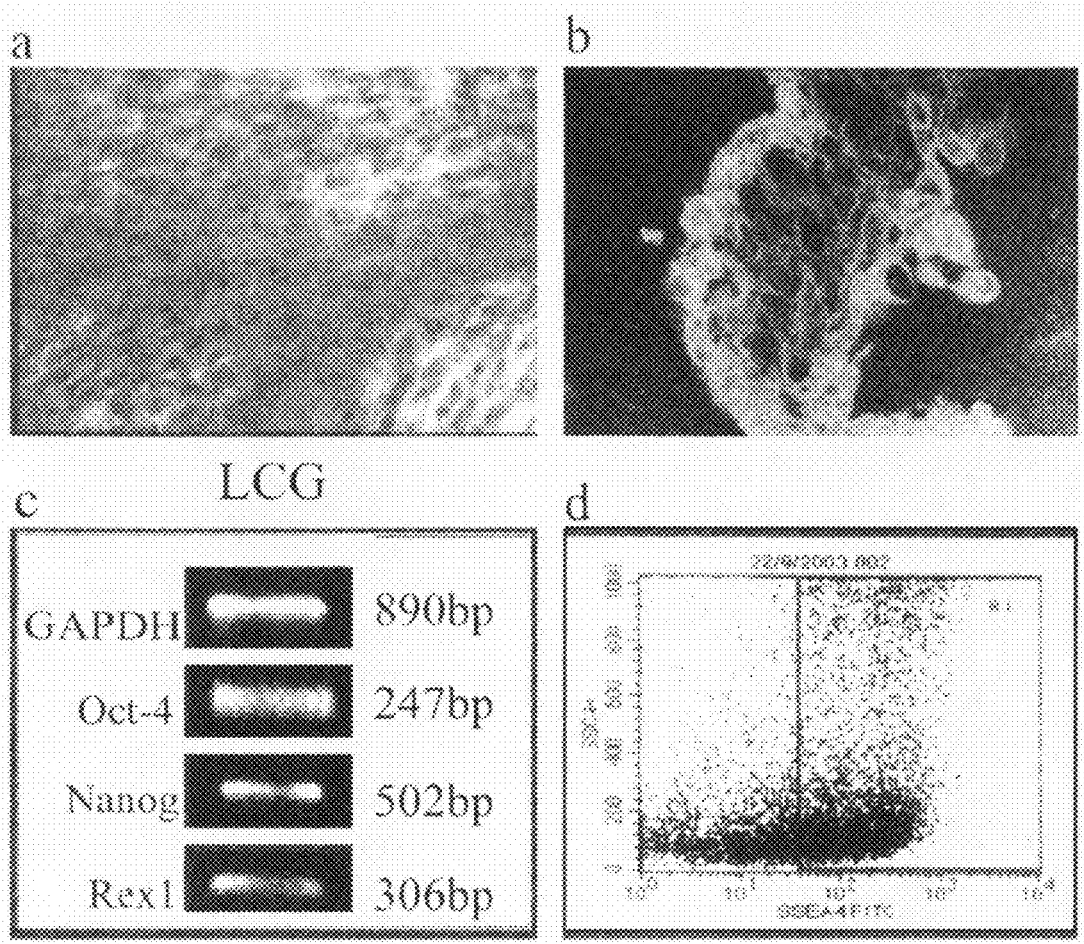
FIG. 1. Limbal composite grafts (LCG): (a) H & E stained LCG (whole mount); (b) LCG probed using immunofluorescence for SSEA-4 antigen; (c) LCG analysis by RT-PCR for expression of the pluripotent stem cell markers Oct-4, Nanog, and Rex 1, as well as GAPDH as a positive control; and (d) SSEA-4 positive cells isolated from LCG by flow cytometry.

The present disclosure relates to the isolation of mammalian pluripotent embryonic-like stem cells (ELSCs) from non-embryonic cells or tissues. In preferred embodiments, the present disclosure utilizes mammalian eye structures as a source of ELSCs, preferably corneal limbus tissue. In preferred embodiments, the ELSCs are derived from corneoscleral or corneal limbus tissue of a human donor. ELSCs of the present disclosure are particularly advantageous due to several unique properties of these cells: (1) ELSCs are capable of differentiating into cells of a variety of different lineage-committed or differentiated cell and tissue types, including cells and tissues derived from all three germ layers, endoderm, ectoderm, and mesoderm; (2) ELSCs are self-renewing and capable of propagating in culture for at least about 20 to about 100 population doublings or more while maintaining pluripotency, high telomerase activity, and normal karyotype; and (3) ELSCs are capable of forming embryoid-like bodies (ELBs).

The pluripotent ELSCs of the present disclosure are undifferentiated or substantially undifferentiated cells that have the potential to differentiate into almost any cell type. Morphological characteristics of undifferentiated cells are well known to those of skill in the art. For example, human ES cells may be morphologically identified by high nucleus to cytoplasm ratios, prominent nucleoli, and compact colony formation, with often distinct cell borders and colonies that are often flatter than mouse ES cells. Human ES cells are also preferably immunoreactive with markers for human pluripotent ES cells, for example SSEA-3, SSEA-4, GCTM-2 antigen, and TRA 1-60, as described by Thomson et al., (Science 282:1145-1147, 1998) and Reubinoff et al. (Nature Biotech. 18:399-403, 2000). As used herein, "non-embryonic cells or tissues" refer to any cells or tissues that are derived from cells or tissues other than embryonic cells, embryonic tissue, fetal primordial germ cells, or fetal gonadal ridge tissue. In particular, non-embryonic cells or tissues include cells or tissues from adult mammals, and can also include cells or tissues from juvenile mammals. ELSCs can differentiate into cells that are committed to a particular germ lineage but still able to give rise to various progeny cells of different cell types within that lineage, as well as cells that are terminally-differentiated.

ELSCs of the present disclosure can be propagated in an in vitro culture, where they are capable of differentiating cells that are derivatives of each of the three germ layers (ectoderm, mesoderm, and endoderm). As used herein, the term "differentiation" refers to a process whereby undifferentiated pluripotent stem cells or precursors cells acquire a more specialized fate. For example, endodermal cells include but are not limited to epithelial cells (e.g., corneal epithelial cells), hepatocytes, beta islet cells, pancreatic cells (e.g., islet, acinar and ductal cells), parenchymal cells of the trachea, bronchi, lungs, gastrointestinal tract, bladder, pharynx, thyroid, thymus, parathyroid glands, tympanic cavity, pharyngotympanic tube, tonsils, and the like; mesodermal cells include but are not limited to myocytes (e.g., smooth muscle, skeletal muscle, cardiac myocytes, cardiomyocytes), adipocytes (e.g., white fat and brown fat adipocytes), chondrocytes, hematopoietic cells (e.g., erythrocytes), lymphocytes, monocytes, macrophages, plasma cells, B cells, natural killer cells and mast cells, endothelial cells, microglia, dendritic cells, megakaryocytes, osteoblasts, osteoclasts, chondroclasts, lymphoid cells, and cells of the tonsils, spleen, kidney, ureter, bladder, testes, ovaries, uterus, and the like; and ectodermal cells include but are not limited to neurons (e.g., dopaminergic, GABAergic, serotonergic, glutamatergic, and motor neurons), glial cells (e.g., oligodendrocytes, astrocytes), epithelial cells, ependymal cells, retinal cells, pineal body cells, posterior pituitary cells, ganglia, peripheral nerve cells, Schwann cells, sensory nerve endings, adrenal medulla, melanocytes, mesenchymal cells, parafollicular "C" (calcitonin secreting) cells, enterochromaffin cells, and cells of the heart valves, heart outflow tract, epidermis, hair, nails, sweat glands, salivary glands, sebaceous glands, mammary glands, anterior pituitary, inner ear, lens of the eye, and the like.

ELSCs are also capable of forming embryoid-like bodies (ELBs) in culture, for example in suspension culture. As used herein, the term "embryoid-like bodies" or "ELBs" refer to an aggregation of differentiated cells generated when pluripotent ELSCs are grown in suspension culture, or overgrow in monolayer cultures. ELBs may also have undifferentiated cells in the aggregation of cells. ELBs typically contain cells derived from all three germ layers, ectoderm, mesoderm and endoderm. Functionally, ELBs may be similar or identical to embryoid bodies generated in culture from ES cells, for example human ES cells. Embryoid bodies and ELBs are distinguished from each other in the present disclosure primarily by source, i.e., embryoid bodies are derived from ES cells, while ELBs are derived from ELSCs.

The present disclosure further describes the isolation of pluripotent ELSCs and uses of those cell lines. The use of ELSCs as a source of pluripotent stem cells has numerous advantages. First, the use of ELSCs does not raise many of the ethical concerns that are associated with research using cells derived from embryonic or fetal cells and tissue. Second, the use of ELSCs may make autologous pluripotent stem cells available for medical therapies as the source of differentiated cells and tissues without the intermediate step of cloning. It is generally desirable that transplanted cells or tissues be genetically identical to the recipient of the transplant in order to avoid problems with tissue rejection. However, it is not generally possible to obtain ES cells that are genetically identical to a patient in need of treatment. The use of ELSCs can surmount this problem if the donor of the ELSCs is also the recipient of transplanted cells or tissue derived from the ELSCs.

While adult stem cells have been previously isolated, none of these adult stem cell lines have had the characteristics of the ELSCs of the present disclosure. For example, previously isolated adult stem cell lines have generally only been able to differentiate into a few cell types, unlike the ELSCs of the present disclosure. In a preferred embodiment of the present disclosure, ELSCs are derived from corneal limbus tissue, which is a safe, simple, and efficient source of pluripotent ELSCs. Therefore, the present disclosure obviates the problems associated with conventional sources of pluripotent stem cells.

A significant advantage of the use of corneal limbal tissue as a source of ELSCs is the relative ease in obtaining corneal limbal tissue from a donor. The process requires only minor surgery, unlike the more invasive procedures that may be used to obtain other types of adult stem cells. The corneal limbal tissue is found in the cornea, which is a transparent, avascular tissue that is located at the outer surface of the anterior eye. It provides protection from environmental insult, and allows for the efficient transmission of light into the eye. The cornea is comprised of two main compartments: (1) the anterior non-cornified stratified squamous epithelial layer and (2) the underlying substantia propria. The human cornea harbors three known cell types: corneal epithelial cells; stromal keratocytes (corneal fibroblast); and an underlying layer of stromal associated corneal endothelial cells. Corneal epithelium is a cellular multiplayer that is five to seven cells thick and covers the anterior surface of the cornea. Ordinarily, a natural turnover of corneal epithelial cells takes place in which superficial epithelial cells are shed from the epithelial surface and replaced by those from below. Basal epithelial cells, migrating inward from the periphery, replenish the population of deeper corneal epithelial cells.

Corneal limbus (also known as corneoscleral limbus) is an annular transitional zone approximately 1 mm wide between the cornea and the bulbar conjunctiva and sclera. It appears on the outer surface of the eyeball as a slight furrow marking the line between the clear cornea and the sclera. It is highly vascular and is involved in the metabolism of the cornea. Limbal and conjuctival epithelial cells, together with a stable pre-ocular tear film maintain the integrity of the cornea. While it is known that the source of the replenished corneal epithelial cells are adult stem cells, the exact location and properties of these cells were unknown. The adult stem cells previously isolated from the eye are P-63 positive, and are responsible for maintaining corneal integrity (Pellegrini et al., (2001) Proc. Acad. Natl. Sci. USA, 98:3156-61). The plasticity of these corneal stem cells was recently reported by Seigel et al. (Mol. Vis. 9:159-63, 2003). The existence of a second population of stem cells that are pluripotent and have similar properties to ES cells was unknown. The present disclosure describes the localization of ELSCs of the eye to the corneoscleral limbus. A typical procedure for isolating corneal limbal tissue is to surgically remove a small biopsy consisting of 2-3 mm of limbal tissue from the superior or temporal quadrant of the corneal surface of the donor's eye. Procedures for obtaining such biopsies from the corneal limbus are known to those of skill in the art.

After limbal tissue is biopsied from a donor, it is placed in culture, preferably on an extracellular matrix or bio-coated surface, for example extracellular matrix or bio-coated petri dishes. Examples of extracellular matrices useful for culturing limbal tissue include but are not limited to Matrigel™ and its equivalents, mammalian amniotic membrane, laminin, collagen-IV, poly-L-lysine, gelatin, poly-L-ornithin, fibronectin, or platelet derived growth factor (PDGF), either alone or in combination with other extracellular matrix materials. Matrigel™ and human amniotic membrane are particularly preferred for culturing biopsied limbal tissue. Preferred methods of using extracellular matrix materials are described in the examples below. With bio-coated surfaces, a preferred method of culturing the limbal tissue is to subject the explants to dry incubation for several minutes on a bio-coated tissue culture plate. The explants are then affixed to the tissue culture dish with a small amount of culture medium so that they stick to the bio-coated tissue culture surface. After several hours to a day, media is gently added and cells are incubated for approximately 4-5 days at 37° C. in a $CO_2$ incubator, changing the media every alternate day.

The preferred media used for culturing the cells of the limbal tissue is Dulbecco's Modified Eagles Medium (DMEM) or DMEM:F-12 (1:1), preferably supplemented with a nutrient serum, for example a serum or serum-based solution that supplies nutrients effective for maintaining the growth and viability of the cells (e.g., knock-out serum or heat-inactivated human serum), as well as growth factors. As used herein, the term "growth factor" refers to proteins that bind to receptors on the cell surface with the primary result of activating cellular proliferation and differentiation. The growth factors used for culturing limbal tissue are preferably selected from epidermal growth factor (EGF), basic fibroblast growth factor (bFGF), leukemia inhibitory factor (LIF), insulin, sodium selenite, human transferrin, or human leukemia inhibitory factor (hLIF), as well as combinations thereof. However, any suitable culture media known to those of skill in the art may be used. In certain embodiments, the limbal cells are treated with cytokines or other growth factors which cause the ELSCs to preferably proliferate in the culture.

After the limbal cells are cultured for several days, preferably 7 to 21 days or until the cells become confluent, ELSCs can be isolated from the culture. In preferred embodiments, the limbal cells are first dissociated from the extracellular matrix, preferably through enzymatic digestion, for example using trypsin-EDTA or dispase solutions. The pluripotent ELSCs can be isolated from the other limbal cells in the culture using a variety of the methods known to those of skill in the art such as immunolabeling and fluorescence sorting, for example solid phase adsorption, FACS, MACS, and the like. In preferred embodiments, the ELSCs are isolated through sorting, for example immunofluorescence sorting of certain cell-surface markers. Two methods of sorting well known to those of skill in the art are magnetic-affinity cell sorting (MACS) and fluorescence-activated cell sorting (FACS).

Sorting techniques such as immunofluorescence-staining techniques involve the use of appropriate stem cell markers to separate ELSCs from other cells in the culture. Appropriate stem cell markers that may be used to isolate ELSCs from cultured limbal cells include but are not limited to SSEA-4, SSEA-3, CD73, CD105, CD31, CD54, and CD117. In preferred embodiments, pluripotent ELSCs are isolated by MACS through the use of a cell surface marker such as SSEA-4. By this means, enriched populations of cell-surface marker positive ELSCs are obtained from the mixed population of limbal cells. Alternatively, the cells can be sorted to remove undesirable cells by selecting for cell-surface markers not found on the pluripotent ELSCs. In the case of ELSCs isolated from limbal tissue, the ELSCs were found to be negative for the following cell-surface markers: CD34, CD45, CD14, CD133, CD106, CD11c, CD123, and HLA-DR.

The enriched ELSCs cultures obtained by sorting have at least about 10%, 20%, 30%, 40%, 50%, 60%, 70%, 80%, 90%, 95%, 98%, or 99% pluripotent ELSCs. In preferred embodiments the isolated cells will be at least about 50%, 70%, 80%, 90%, 95%, 98%, or 99% SSEA-4 positive ELSCs cells. In alternative embodiments, mixed cell cultures containing pluripotent ELSCs are screened for the presence of ELSCs that express certain gene markers. In the case of mixed limbal cell cultures, populations of pluripotent ELSCs can be identified by the expression of gene markers such as OCT-4, Nanog, TDGF, UTX-1, FGF-4, Sox 2, Rex 1, as well as other gene marker of undifferentiated cells.

The ELSCs isolated from the limbal cell culture are cultured or passaged in an appropriate medium to allow the ELSCs to remain in a substantially undifferentiated state. Although colonies of undifferentiated ELSCs within the population may be adjacent to neighboring cells that are differentiated, the culture of ELSCs will nevertheless remain substantially undifferentiated when the population is cultured or passaged under appropriate conditions, and individual undifferentiated ELSCs constitute a substantial proportion of the cell population. ELSCs cultures that are substantially undifferentiated contain at least about 20% undifferentiated ELSCs, and may contain at least about 40%, 60%, 80%, or 90% ELSCs. For example, ELSCs must be kept at an appropriate cell density and repeatedly dissociated and subcultured while frequently exchanging the culture medium to prevent them from differentiating. When ELSCs are passaged they may be dispersed into small clusters or into single-cell suspensions. Typically, a single cell suspension of cells is achieved and then seeded onto another tissue culture grade plastic dish.

For general techniques relating to cell culture and culturing ES cells, which can be applied to culturing ELSCs, the practitioner can refer to standard textbooks and reviews, for example: E. J. Robertson, "*Teratocarcinomas and embryonic stem cells: A practical approach*" ed., IRL Press Ltd. 1987; Hu and Aunins (1997), Curr. Opin. Biotechnol. 8:148-153; Kitano (1991), Biotechnology 17:73-106; Spier (1991), Curr. Opin. Biotechnol. 2:375-79; Birch and Arathoon (1990), Bioprocess Technol. 10:251-70; Xu et al. (2001), Nat. Biotechnol. 19(10):971-4; and Lebkowski et al. (2001) Cancer J. 7 Suppl. 2:S83-93, each incorporated herein by reference.

The isolated ELSCs are cultured in an appropriate cell culture medium such as DMEM or DMEM:F-12 medium, preferably supplemented with a nutrient serum, for example a serum or serum-based solution that supplies nutrients effective for maintaining the growth and viability of the cells (e.g., knock-out serum or heat-inactivated human serum), as well as growth factors. In preferred embodiments, the medium is supplemented with growth factors such as EGF, basic FGF, LIF, insulin, transferrin, sodium selenite, and fibronectin. In some embodiments, the ELSCs are cultured on a feeder layer. Methods for culturing pluripotent stem cells on feeder layers are well known to those of skill in the art (U.S. Pat. No. 5,843,780, WO 99/20741, incorporated herein by reference). In other embodiments, the ELSCs are cultured on an extracellular matrix. An extracellular matrix provides conditions for supporting cell growth, for example similar to the conditions provided by feeder cells. ELSCs may also be grown in the presence of conditioned medium that can support growth of ELSCs cells, for example in a feeder-free culture. Conditioned medium is prepared by culturing a first population of cells in a medium for a sufficient period of time to produce "conditioned" medium which will support the culturing of ELSCs without substantial differentiation.

The isolated ELSCs can be serially passaged for at least 20, 40, 60, 80, 100 or more passages, without substantially differentiating. ELSCs also can be frozen for further use at various time points without loss of differential potential, i.e., the cells will retain the ability to differentiate into derivative of endodermal, ectodermal, or mesodermal lineage under appropriate conditions. In preferred embodiments, the isolated ELSCs retain high telomerase activity and normal karyotypes for at least 20, 40, 60, 80, 100 or more passages.

In another embodiment, isolated pluripotent ELSCs are identified and characterized by the ability to form ELBs in culture, for example in suspension culture. Preferably the ELBs can be further cultured to differentiate into cells of ectodermal, mesodermal, and endodermal lineages. Methods for culturing pluripotent stem cells to generate embryoid bodies are disclosed in U.S. Pat. No. 6,602,711, incorporated herein by reference. These same methods can also be used to generate ELBs from the ELSCs disclosed herein. For example, ELSCs are dissociated using trypsin, and cultured on bacteriological plates that have a non-adhesive surface, thereby preventing attachment of the ELSCs to the surface of the plate. The ELSCs are preferably cultured in an appropriate cell culture medium such as knockout DMEM or DMEM: F-12 medium, preferably supplemented with a nutrient serum, for example a serum or serum-based solution that supplies nutrients effective for maintaining the growth and viability of the cells (e.g., fetal calf serum or fetal bovine serum), as well as growth factors. In preferred embodiments, the medium is supplemented with growth factors such as insulin, transferrin, or sodium selenite. The cells are cultured until they form ELBs. Preferably the ELBs are cultured until they reach sufficient size or desired differentiation, for example after 3-10 days of culture, preferably 4-14 days. When ELBs are subsequently cultured to differentiate into particular cell types, the ELBs are allowed to grow to a sufficient size to facilitate differentiation into the selected cell type. The ELBs may be plated onto a substrate, for example a substrate coated with extracellular matrix components, including but not limited to poly-L-lysine, poly-L-ornithine, laminin, collagen, fibronectin, Matrigel®, or combinations thereof. The ELBs may be plated directly onto a substrate with or without dispersing the cells.

ELSCs disclosed herein can be utilized for various applications, such as therapeutic and diagnostic applications, as well as for in vitro and in vivo assessment and screening of various compounds such as small molecule drugs for their effects on these cells, as well as differentiated cells derived from ELSCs. The differentiated cells may be either lineage-committed progenitor cells, or terminally-differentiated cells. Examples of differentiated cell types that may be derived from pluripotent ELSCs include but are not limited to neuronal cells, corneal cells, osteoblasts, chondrocytes, adipocytes, beta-islets, cardiomyocytes, hepatocytes, and the like. The ELSCs and cells and tissues differentiated therefrom of the present disclosure can be used to treat any subject in need of treatment, including but not limited to humans, primates, and domestic, farm, pet, or sports animals, such as dogs, horses, cats, sheep, pigs, cattle, rats, mice, and the like. These cells can also be used to prepare cDNA expression libraries to analyze the expression patterns of ELSCs as well as cells derived therefrom, and to prepare monoclonal or polyclonal antibodies that are specific to markers for the particular cells used, using techniques that are well known to those of skill in the art.

These cells can also be use therapeutically to the benefit of individuals suffering from debilitating diseases, conditions, injuries, and disorders, for example in tissue reconstitution or regeneration in subjects such as human patients. As used herein, the terms "therapeutically", "to treat", "treatment", or "therapy" refer to both therapeutic treatment and prophylactic or preventative measures. Therapeutic treatment includes but is not limited to reducing or eliminating the symptoms of a particular disease, condition, injury or disorder, or slowing or attenuating the progression of, or curing an existing disease or disorder. Subjects in need of such therapy will be treated by a therapeutically effective amount of such cells to tissues to restore or regenerate function. As used herein, a "therapeutically effective amount" of cells or tissues is an amount sufficient to arrest or ameliorate the physiological effects in a subject caused by the loss, damage, malfunction, or degeneration of particular cell-types or tissue-types. The therapeutically effective amount of cells or tissues used will depend on the needs of the subject, the subject's age, physiological condition and health, the desired therapeutic effect, the size of the area of tissue that is to be targeted for therapy, the site of implantation, the extent of pathology, the chosen route of delivery, and the treatment strategy. These cells or tissues may be administered to the patient in a manner that permits the cells or tissue to graft to the intended tissue site and reconstitute or regenerate the functionally deficient area.

The following is a brief but by no means exhaustive list of human diseases and conditions potentially treatable through the administration of ELSCs or differentiated cells or tissues derived therefrom: neurodegenerative disorders and neuronal diseases such as Parkinson's disease, Alzheimer's disease, Huntington's disease, Lewy body dementia, pancreatic diseases such as diabetes and juvenile onset diabetes mellitus, cardiovascular and heart diseases such as cardiac infarcts, Acquired Immunodeficiency Disease Syndrome (AIDS), hematopoietic diseases such as lymphoma and leukemia, cerebellar ataxia, progressive supranuclear palsy, amyotrophic lateral sclerosis (ALS), epilepsy, multiple sclerosis, burns, stroke, ischemia, trauma to the nervous system, neurotoxic injury, and spinal cord injuries.

ELSCs of the present disclosure may be induced to differentiate by any appropriate method known to those of skill in the art. Many such methods are well known to those of skill in the art for differentiating ES cells or adult stem cells into specific cell types, for example neuronal precursor cells, neuronal cells, or glial cells (U.S. Ser. No. 09/970,382, WO 01/88104, WO 03/000868, WO 01/68815, WO 01/83715, and U.S. Ser. Nos. 10/157,288 and 10/127,740), hematopoietic cells (U.S. Pat. No. 6,280,718, WO 01/34776), cardiomyocytes (WO 03/006950), hepatocytes (U.S. Pat. Nos. 6,458, 589 and 6,506,574), endothelial cells (WO 03/40319), insulin-producing cells (WO 02/92756), and endocrine cells (WO 02/59278), all of which are specifically incorporated herein by reference. Although these methods were originally adapted for differentiating ES cells or adult stem cells into specific cell types, they may also be adapted to differentiate the ELSCs described herein. These methods can include differentiation through the formation of colonies, ELBs, or other aggregates (WO 01/62899, specifically incorporated herein by reference), as well as methods promoting differentiation into certain cell lineages by withdrawing serum or factors that inhibit differentiation and/or adding factors that promote differentiation. Differentiation of cells may also be facilitated by the use of particular extracellular matrices, for example poly-o-orinthine, laminin, or Matrigel™. ELSCs can also be differentiated directly into committed precursor cells or fully differentiated cells, for example without forming ELBs as an intermediate step.

Preferred methods of inducing differentiation of ELSCs include the use of differentiation agents, including but not limited to progesterone, putrescine, laminin, insulin, sodium selenite, transferrin, neurturin, sonic hedgehog (SHH), noggin, follistatin, retinoic acid, epidermal growth factor (EGF), any type of fibroblast growth factor, cytosine β-d-Arabino furanoside (Ara-C), growth and differentiation factor 5 (GDF-5), members of the neurotrophin family (nerve growth factor (NGF), neurotrophin 3 (NT-3), neurotrophin 4 (NT-4), brain derived neurotropic factor (BDNF)), transforming growth factor α (TGF-α), transforming growth factor beta-1 (TGF β1), transforming growth factor beta-3 (TGF β3), platelet-derived growth factor (PDGF), insulin-like growth factor (IGF-1), bone morphogenic proteins (BMP-2, BMP-4), glial cell derived neurotrophic factor (GDNF), midkine, ascorbic acid, ascorbic acid 2 phosphate, dibutyryl cAMP, dopamine, ligands to receptors that complex with gp130 (e.g., LIF, CNTF, SCF, IL-11, and IL-6), insulin-transferrin-selenious acid (ITS), dexamethasone, sodium butyrate, dimethyl sulfoxide (DMSO), N-acetyl Cysteine, insulin-like growth factor I or II (IGF-I or IGF-II), β glycerophosphate, 5-Azadeoxy-cytidine, oncostatin, hepatocyte growth factor (HGF), nicotinamide, or combinations thereof. As used herein, the term "fibroblast growth factor" or "FGF" refers to any suitable fibroblast growth factor, derived from any organism that expresses such factors, and functional fragments thereof. A variety of FGFs are known to those of skill in the art, and include but are not limited to, FGF-1 (acidic fibroblast growth factor), FGF-2 (basic fibroblast growth factor), FGF-3 (int-2), FGF-4 (hst/K-FGF), FGF-5, FGF-6, FGF-7, FGF-8, and FGF-9. Differentiation nutrient mediums may also contain additives that help sustain cultures of neural cells, for example N2 and B27 additives (Gibco). Pluripotent ELSCs can be induced to differentiate in various available culture media, including but not limited to DMEM, DMEM-F-12, MCDB, Neurobasal medium, neurturin, N2, B27, and the like, or combinations thereof.

The presence of differentiated cells in a cell culture can be determined by any one of many methods known to those of skill in the art. For example, determination of differentiated cells can be accomplished by methods such as flow cytometry, immunochemistry, immunofluorescence staining, or other staining techniques, for example Von Kossa staining of osteoblasts, Alcian Blue staining of chondrocytes, or Oil Red-O staining of adipocytes, to detect the presence of cell surface markers, proteins, or other types of genetic markers. Alternately, identifying differentiated cells may be accomplished by detecting expression of certain genes or gene products such as RNA or proteins using RT-PCR, HPLC, and the like.

The following is an exemplary list of methods for differentiating pluripotent ELSCs into particular cell types. This list is by no means exhaustive, and is intended for illustrative purposes only. In one specific embodiment, pluripotent ELSCs can be induced to differentiate into neurons by culturing the cells in a neurobasal medium supplemented with B-27, N2, insulin-transferrin, and selenite in the presence of retinoic acid, basic FGF, and Ara C for approximately 4 to 14 days. In another specific embodiment, pluripotent ELSCs can be induced to differentiate into hepatocytes directly or by exposing ELBs to acidic FGF, basic FGF, HGF, oncostatin, dexamethasone, insulin, transferrin-selenious acid (ITS), DMSO, 5-azacytidine, sodium butyrate, or combinations thereof. In another specific embodiment, pluripotent ELSCs can be differentiated into cardiomyocytes directly or by exposing ELBs to TGF-β1, IGF-I, IGF-II, BMP-4, basic FGF, FGF-4, PDGF-BB, 5-aza-deoxycytidine, insulin, EGF, or combinations thereof. In still another specific embodiment, pluripotent ELSCs can be differentiated into beta-islet cells either directly or by exposing ELBs to $N_2$, $B_{27}$, nicotinamide, basic FGF, TGF-β1, or combinations thereof.

In a further specific embodiment, pluripotent ELSCs can be differentiated into chondrocytes either directly or by exposing ELBs to TGFβ3, ascorbic acid 2 phosphate, or combinations thereof. In another specific embodiment, pluripotent ELSCs can be differentiated into osteoblasts directly or by exposing ELBs to dexamethasone, β-glycerophosphate, ascorbic acid 2 phosphate, hydrocortisone, or combinations thereof. In yet another specific embodiment, pluripotent ELSCs can be differentiated into adipocytes directly or by exposing ELBs to dexamethasone, isobutylmethylxanthine (IBMX), indomethacin, insulin, or combinations thereof. In a further specific embodiment, pluripotent ELSCs can be differentiated into myocytes directly or by exposing ELBs to 5-Azacytidine, PDGF-BB, or combination thereof. The present disclosure also provides a method of cryopreservation of pluripotent ELSCs, for example, wherein the cells are cryopreserved in 10% dimethyl sulfoxide (DMSO) or another appropriate medium and stored in liquid nitrogen.

The present disclosure also contemplates the use of pluripotent ELSCs for cell-based therapies. As reported in the literature, the ability to regenerate human tissues that are substantially damaged due to disease or injury is reduced significantly in adults. Pluripotent ELSCs disclosed herein may be induced to terminally differentiate into appropriate cell or tissue types, or to differentiate into appropriate lineage-committed progenitor cells, which can then be administered or transplanted into a mammalian subject for cell replacement therapy or tissue regeneration. Alternatively, ELSCs may be directly administered to a subject. Therefore, the methods of the present disclosure may be useful in the treatment of many diseases, injuries, or other detrimental condition. Pluripotent ELSCs of the present disclosure can be induced to differentiate either in vitro or in vivo.

ELSCs generated according to the present disclosure can also be used to study the cellular and molecular biology of development, functional genomics, as well as the generation of differentiated cells for use in therapeutic or prophylactic transplantation, treatment, drug screening, or in vitro drug discovery. For example, the ELSCs can be used for genomic analysis, to produce mRNA, cDNA, or genomic libraries, to produce specific polyclonal or monoclonal antibodies, including but not limited to humanized monoclonal antibodies (WO 01/51616, specifically incorporated herein by reference), or to screen for the effects of different test compounds or biologically active molecules on ELSCs and cells or tissues derived therefrom, such as pharmaceutical compounds in drug research. The test compounds or biologically active molecules screened may be derived for example from plants, plant-based extracts, or synthetic sources. ELSCs can also be used to screen for factors (such as small molecule drugs, peptides, polynucleotides, and the like) or conditions (such as cell culture conditions or manipulations) that affect the characteristics of ELSCs in culture, and the differentiation of ELSCs into various specific cell and tissue types.

Differentiated cells derived from ELSCs, for example neuronal cells, beta-islets, cardiomyocyte, hepatocyte, corneal cells, osteoblasts, chondrocytes, and adipocytes, can be used to generate human body organs by 3-D reconstruction, for example tissues in the human brain may be reconstructed by 3-D culturing of the neurons derive from human ELSCs. Similarly, other human body organs or parts such as liver, heart, kidney, skin, eye, ear, and the like may be derived and reconstructed from pluripotent ELSCs. ELSCs of the present disclosure may also be used as carrier vehicles for various therapeutically active molecules or genes to be delivered at various sites of the human body, for example by genetically manipulating and differentiating the ELSCs as required, and delivering the cells or tissue to a target site in a donor for gene therapy. The present disclosure therefore provides methods of using pluripotent ELSCs with their unique capability to differentiate into cells of all three germ layer lineages for pharmaceutical interventions and for human-based cell assays for drug discovery, analysis, and testing.

The following examples are included to demonstrate preferred embodiments of the disclosure. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

1) Collection of Limbal Tissue Biopsies

Prior to initiating the collection of limbal tissue biopsies from human patients, Institutional Review Board approval was obtained. Informed consent was obtained from each patient and donor, and all human subjects were treated according to the Helsinki Accord. A 2-3 mm limbal biopsy of the donor eye was collected surgically from superior or temporal quadrants of the corneal surface by lamellar keratectomy. After excision, biopsies were immediately placed in a 2 ml transport vial filled with transport medium. The transport medium consisted of Dulbecco's Modified Eagles Medium (DMEM) and Ham's F-12 Medium (DMEM:F-12; 1:1) supplemented with 5% fetal bovine serum (FBS) or 5% human serum collected from cord blood, 0.5% dimethyl sulphoxide (DMSO), 2 ng/ml recombinant human epidermal growth factor (rhEGF), 5 µg/ml insulin, 5 µg/ml transferrin, 5 µg/ml sodium selenite, 0.5 µg/ml hydrocortisone, 0.1 nmol/l cholera toxin A, 50 µg/ml gentamycin, and 1.25 µg/ml amphotericin B. Blood samples were also collected from each donor and transported along with each limbal tissue biopsy to a centrally located cGMP facility. Blood samples were immediately tested for infectious diseases, including Hepatitis B virus (HBV), Hepatitis C virus (HCV), Syphillis, and CMV.

2) Preparation of Extracellular Matrices for Limbal Biopsies

Throughout the studies described herein, suitable extracellular matrix carriers such as Matrigel™, fibrinogen, PDGF, laminin, EGF, collagen V, or human amniotic membrane were used to culture limbal tissue biopsies. In certain studies, the extracellular matrix carrier was treated with attachment factors such as laminin, collagen V, PDGF, EGF, or fibrinogen, either singly or in combination, along with growth factors such as EGF, insulin-like growth factor-1 (IGF-1), insulin, either singly or in combination. In the present disclosure, Matrigel™ (BD Biosciences) is the preferred extracellular matrix carrier.

To prepare Matrigel™ coated tissue culture plates, Matrigel™ was slowly thawed overnight at 4° C. to avoid the formation of a gel. After complete thawing, 10 ml of cold knockout DMEM was added to the bottle containing 10 ml Matrigel™ and mixed. The mixture was kept on ice, mixed well, and aliquots of 1 ml were prepared and stored at −20° C. until needed for coating plates. As needed, each Matrigel™ aliquot was slowly thawed at 4° C. for at least 2 hours to avoid the formation of a gel. The aliquot was then diluted 1:15 in cold knockout DMEM, and 1 ml of Matrigel™ solution was added to coat 35 mm or 60 mm plates. After pouring the solution into the plates, the plates were allowed to set for 1-2 hours at room temperature or overnight at 4° C. After setting, any remaining Matrigel™ solution was removed from the plate prior to use, and the plates were washed with knockout DMEM prior to use.

3) Preparation of Amniotic Membrane Cultures for Limbal Biopsies

Amniotic membrane cultures were used to culture limbal tissue biopsies isolated from human subjects. The preparation of these amniotic membrane culture began with the collection of human placental membranes. Placental membranes were collected from elective Cesarean section operations and transported to laboratory facilities in a transport medium consisting of Dulbecco's phosphate buffered saline (DPBS) supplemented with 50 unit/ml penicillin, 50 µg/ml streptomycin, 50 µg/ml neomycin, and 2.5 µg/ml amphotericin B. Placental membrane was transported to the laboratory within 3 hours of surgery. Blood samples were also collected from each donor and sent for infectious disease diagnostic tests as described above.

Once received, the placenta was washed with washing medium to remove mucus and blood clots. The washing medium consisted of Dulbecco's phosphate buffered saline (DPBS) supplemented with 50 unit/ml penicillin, 50 µg/ml streptomycin, 100 µg/ml neomycin, and 2.5 µg/ml amphotericin B. Placental tissue was removed from the amniotic membrane using sterile scissors, and the amniotic membrane was washed thoroughly at least 7 times to remove substantially all blood clots. Next, the chorion was peeled off of the amniotic membrane with blunt forceps, and the epithelial side of the amniotic membrane was washed 5 times with the washing medium. The amniotic membrane was then placed on a sterile nitrocellulose membrane with the epithelial side of the membrane facing up. The membrane was cut into 5 cm×5 cm area pieces and each piece was placed in a cryo-vial filled with freezing medium consisting of 50% glycerol in DMEM. Each batch of processed amniotic membrane was checked for sterility, as well as the absence of mycoplasma or endotoxin contamination before being used for limbal culture. The pieces of amniotic membrane were each stored at −80° C.

Amniotic membrane cultures for culturing limbal tissue biopsies were prepared from these pieces of amniotic membrane by first thawing the pieces at room temperature for 20 minutes. Each amniotic membrane was then carefully removed from the nitrocellulose membrane using blunt forceps, preferably without tearing the surface, and placed on a sterile glass slide in a 100 mm petri plate. Next, a small volume of trypsin (1.0-1.5 ml of 0.05% Trypsin-EDTA) was added to cover the amniotic membrane, and the membrane was incubated at 37° C. for 30 minutes. After incubation, the epithelial layer of the amniotic membrane was scraped off with a cell scraper under sterile aseptic conditions. The amniotic membrane was then washed 3 times with washing solution. The processed and treated amniotic membrane, which functions as an extracellular carrier matrix in culture, was placed on a culture plate with a 0.4 µM track-etched polyethylene terephthalate (PET) membrane insert (Falcon, USA, 3090). The amniotic membrane was fastened to the PET insert, for example by using number 10 Ethilon non-absorbent suture or by using a medical grade silicon O-ring.

Regardless of the means, the amniotic membrane should be spread on the membrane insert in such a way that the denuded epithelial side of the membrane faces the inner side of the insert and the stromal side of the membrane faces out of the insert. The amniotic membrane was stretched uniformly before being secured to the insert, for example by inserting the silicon O-ring into the bottom of the amniotic membrane, or suturing the amniotic membrane to the basement membrane of the insert. The entire set-up was incubated in a 6-well dish filled with culture medium for at least 2 hours in DMEM/F12 (Gibco-BRL) media supplemented with 10% FBS (ES tested) (Hyclone), 5 µg/ml transferrin (Gibco), 0.1 µg/ml cholera toxin (Sigma), 50 U/ml penicillin-streptomycin (Sigma), 5 µg/ml gentamicin (Sigma), 5 ng/ml Na-selenite (Sigma), 10 ng/ml EGF (Sigma), and 0.5% DMSO (Sigma). The amniotic membrane was washed two times with culture medium and again incubated in culture medium for 30 minutes, after which the amniotic membrane was ready for culturing limbal tissue biopsies.

4) Culturing of Limbal Biopsies to Produce Limbal Composite Grafts

Limbal tissue from the limbal biopsies was initially washed several times with culture medium DMEM/F12 (Gibco-BRL) media supplemented with 10% FBS (ES tested) (Hyclone), 5 µg/ml transferrin (Gibco), 0.1 µg/ml cholera toxin (Sigma), 50 U/ml penicillin-streptomycin (Sigma), 5 µg/ml gentamicin (Sigma), 5 ng/ml Na-selenite (Sigma), 10 ng/ml EGF (Sigma), and 0.5% DMSO (Sigma). The biopsies were then trimmed of any sclera and conjunctiva tissues and cut into 6 to 7 pieces. These limbal tissue pieces were subsequently cultured on Matrigel™ coated plates or on amniotic membrane cultures, which were prepared as described above. Some of the limbal tissue pieces were enzymatically treated with 0.25% trypsin-EDTA (Gibco-BRL, USA) for 30 minutes, while others were treated with 0.25% trypsin-EDTA overnight at 4° C. The epithelial layer of each biopsy piece was removed using blunt forceps, and the stromal were cultured cells on Matrigel™-coated 35 mm plates in culture medium consisting of Dulbecco's Modified Eagles Medium (DMEM) and F-12 (DMEM:F-12; 1:1) supplemented with 10% knock-out serum or 10% heat-inactivated human serum collected from cord blood, 0.5% dimethyl sulphoxide (DMSO), 2 ng/ml recombinant human epidermal growth factor (rhEGF), 5 µg/ml insulin, 5 µg/ml transferrin, 5 µg/ml sodium selenite, 0.5 µg/ml hydrocortisone, 4 ng/ml bFGF, 10 ng/ml hLIF, 50 µg/ml gentamycin, and 1.25 µg/ml amphotericin B. The entire culture process to generate limbal composite grafts was carried out at 37° C. in air (5% $CO_2$) for 7 to 21 days or until the cells became confluent, with the culture medium being changed every alternate day.

To determine whether the limbal composite grafts (LCG) contained pluripotent ELSCs, the LCGs were analyzed by immunofluorescence and flow cytometry to detect the presence of the cell surface marker SSEA-4, which is a marker for human pluripotent ES cells. FIG. 1(a) shows Hematoxylin and Eosin (H & E) staining of a LCG (whole mount). Hematoxylin stains negatively charged nucleic acids such as nuclei and ribosomes blue, while Eosin stains proteins pink. As shown in FIG. 1(b), when a LCG is exposed to an SSEA-4 antibody (1:100 dilution), the LCG is clearly positive for SSEA-4, as indicated by green immunofluorescence. Molecular characterization of the LCG was also performed using RT-PCR analysis to detect OCT-4, Nanog, and Rex-1 expression, each of which are pluripotency markers that are down-regulated upon differentiation. FIG. 1(c) shows expression of each of these pluripotent stem cell markers, with GAPDH acting as a positive control. Finally, FIG. 1(d) shows the isolation of SSEA-4 positive cells (63%) from a LCG by flow cytometry after the cells were subjected to magnetic affinity cell sorting (MACS) (see below).

5) Isolation of Pluripotent Embryonic-Like Stem Cells from Limbal Composite Grafts After 7 to 21 days of limbal cell culture, the cultured cells were subjected to magnetic affinity cell sorting (MACS) to isolate pluripotent ELSCs. The cultured cells were first dispersed using 0.05% trypsin-EDTA. The trypsin was neutralized by adding an equal amount of culture medium that contained a trypsin inhibitor or fetal calf serum. The cells were subsequently pipeted into a single cell suspension, and counted using a hemocytometer. Next, the cells were spun down and resuspended to a concentration of $10^7$ cells per 200 µl of PBS. The cells were incubated for 30 minutes at 4° C. with 1 µl of primary antibody SSEA-4 (DSHB, USA; 1:40).

After incubation with SSEA-4 primary antibody, the cells were washed twice with PBS to remove any unbound antibody. A 20 μl suspension of secondary antibody beads (Miltenyi Biotech, Germany; 1:4) that bind to the SSEA-4 primary antibody was added to 200 μl of the cell suspension, mixed well, and incubated at 4° C. for 20 minutes. The cells were washed three times with PBS to remove any unbound secondary antibody.

The cell suspension were then passed through a MACS magnetic column according to the manufacturer's instructions (Miltenyi Biotech, Germany) to isolate SSEA-4 positive cells. The negative fraction was collected first, and the column was washed twice with PBS. Next, the column was removed from the magnet and the positive fraction with SSEA-4 positive cells was collected. The SSEA-4 positive cells, are also pluripotent ELSCs, were washed twice and seeded on an extracellular matrix carrier in culture medium. Preferably, the extracellular matrix carrier was Matrigel™-coated plates and the culture medium was DMEM and F-12 (DMEM:F-12; 1:1), supplemented with 10% knock-out serum or 10% heat-inactivated human serum collected from cord blood, DMSO (0.5%), rhEGF (2 ng/ml), insulin (5 μg/ml), transferrin (5 μg/ml), sodium selenite (5 μg/ml), gentamycin (50 μg/ml) and amphotericin B (1.25 μg/ml), hLIF (10 ηg/ml), and bFGF (4 ηg/ml). The ELSCs were cultured for an additional week at 37° C. in a $CO_2$ incubator or until the cultures became confluent.

After confluence, the ELSCs in culture were dissociated and re-plated on fresh bio-coated tissue culture dishes at a plating dilution of 1:3. The ELSCs were then expanded and serially passaged for at least 100 population doublings. ELSCs that were serially passaged could also be frozen for further use without any loss of differential potential. Telomerase activity was still detected in the cultured cells after 50 passages.

Example 2

Analysis and Characterization of Pluripotent Embryonic-Like Stem Cells

As outlined in Example 1, pluripotent ELSCs were derived from limbal tissue biopsies. Although not wishing to be limited to any particular theory, it appears that corneal limbus has essentially two stem-cell types that are segregated into two zones. The top layer of the limbus is composed mainly of corneal epithelial stem cells that are P-63 positive, while the basal layer is composed mainly of stromal cells. It appears that the pluripotent ELSCs disclosed herein, predominantly reside in the stromal layer, and may migrate towards the epithelial zone as needed.

To better understand the nature of the pluripotent ELSCs derived from limbal tissue, and the undifferentiated status of these cells, ELSCs were analyzed using flow cytometry, immunofluorescence, and molecular analysis for the presence or absence of various cellular markers for undifferentiated and differentiated cells. Karyotype and telomerase activity were also analyzed at various passages to determine whether these cells maintain an undifferentiated state after serial passages.

1) Flow Cytometry Analysis

Only a few cell surface markers that are immunoreactive with pluripotent embryonic stem cells are known. To determine whether the ELSCs isolated herein are also immunoreactive with these cell surface markers, the ELSCs were analyzed for the presence of various cell surface cluster differentiation (CD) markers and stage specific embryonic antigen (SSEA) markers that are usually expressed on pluripotent ES cells. Analysis was carried out after every passage. The presence of the following markers was also analyzed using flow cytometry: SSEA-1, SSEA-3, SSEA-4, CD11c, CD14, CD34, CD45, CD54, CD73, CD105, CD106, CD123, CD133, stem cell factor (SCF), and HLA-DR markers. Antibodies to SSEA-1, SSEA-3, and SSEA-4, and CD markers have previously been used for flow cytometry analysis.

Pluripotent ELSCs isolated in Example 1 were trypsinized after expansion using 0.25% trypsin-EDTA for 2-3 minutes. After inactivation of the trypsin, the cells were passed through a 40 micron filter mesh to remove any remaining cellular clumps that could interfere with staining. The cells were then centrifuged and resuspended in wash buffer at a concentration of $1 \times 10^6$ cells/ml. The wash buffer consisted of phosphate buffer supplemented with 1% fetal bovine serum. Aliquots of $1 \times 10^5$ cells were added to control and test tubes and incubated with the following antibodies, each of which was conjugated with either fluorescein isothiocyanate (FITC) or phycoerythrin (PE): SSEA-1, SSEA-3, SSEA-4, CD11c, CD14, CD31, CD34, CD45, CD54, CD73, CD105, CD106, CD117, CD123, CD133, or HLA-DR antibody. The tubes were vortexed briefly and incubated in the dark for 1 hour at 4° C. The cells were washed 3-4 times with wash buffer and resuspended in 500 μl of wash buffer. Flow cytometry was performed on a FACS Calibur flow cytometer (Becton-Dickinson), and cells were identified by light scatter. Logarithmic fluorescence was evaluated on 10,000 gated events, and control samples were used to adjust the background fluorescence. Analysis was performed using CELL QUEST software (Becton Dickinson). The percent of positive cells was determined with respect to the control tube events. Results are summarized in Table 1 below:

TABLE 1

Results of the various stem cell markers analyzed for pluripotent embryonic-like stem cells by flow cytometry

| SI. No | Markers | Results | % Cells positive |
|---|---|---|---|
|  | SSEA-1 | Negative | 0% |
|  | SSEA-3 | Positive | 19% |
| 1 | SSEA-4 | Positive | 98% |
| 2 | CD11c | Negative | 0% |
| 3 | CD14 | Negative | 0% |
| 4 | CD34 | Negative | 0% |
| 5 | CD45 | Negative | 0% |
| 6 | CD54 | Positive | 51% |
| 7 | CD73 | Positive | 98% |
| 8 | CD105 | Positive | 98% |
| 9 | CD106 | Negative | 0% |
| 10 | CD117 | Positive | 44% |
| 11 | CD123 | Negative | 0% |
| 12 | CD133 | Negative | 0% |
| 13 | HLA-DR | Negative | 0% |
| 14 | CD-31 | Positive | 98% |

Figure 2:
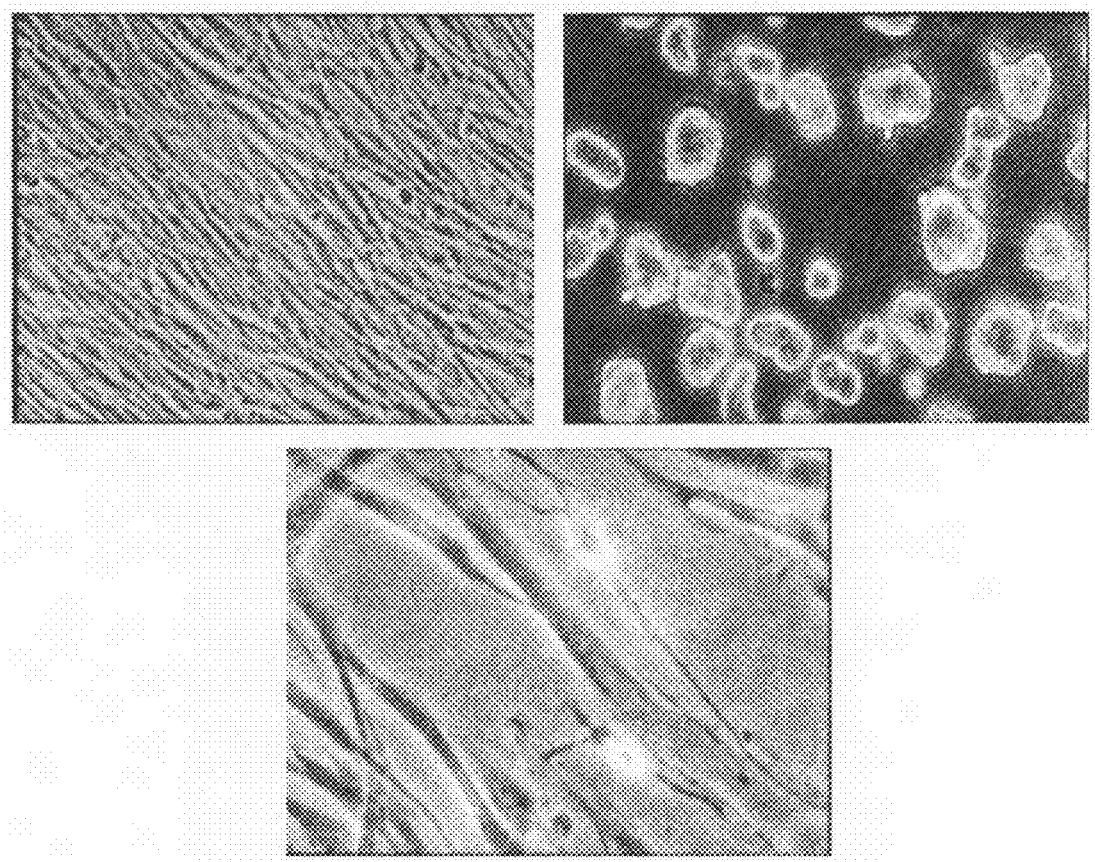
FIG. 2. Immunophenotyping of ELSCs: ELSCs cultured for 20 passages were labeled with FITC-coupled antibodies against SSEA-4, CD105, CD73, CD54, CD45, CD34, CD123, CD133, CD 123, and HLA-DR. The ELSCs demonstrated positive labeling with SSEA-4, CD105, CD73, and CD54 antibodies, indicating that the cells maintain pluripotency after 20 passages, and that ELSCs are not hematopoietic in origin.

Results of immunophenotyping pluripotent ELSCs cultured for 20 passaged are shown in FIG. 2. As outlined above, the ELSCs were labeled with FITC-coupled antibodies against SSEA-4, CD105, CD73, CD54, CD45, CD34, CD123, CD133, CD 123 and HLA-DR. The ELSCs were analyzed using FACS-calibur. The results in FIG. 2 are consistent with the results shown in Table 1. As shown, ELSCs are positive for SSEA-4, CD54, CD73, and CD105 markers, and negative for CD34, CD45, CD106, CD123, CD133, and HLA-DR markers.

Pluripotent ELSCs were found to have similar characteristics to previously isolated primate ES cells derived from the inner cell mass of a blastocyst (U.S. Pat. No. 6,200,806), namely the ELSCs were positive for the stage-specific embryonic antigen markers SSEA-3 and SSEA-4, and negative for the SSEA-1 marker. The expression of SSEA-3 and SSEA-4, and the lack of expression of SSEA-1, in limbal-tissue-derived pluripotent ELSCs is similar to that of human ES cells, indicating that these pluripotent cells may have similar properties.

Pluripotent ELSCs were also analyzed for cluster differentiation markers, and were found to be negative for CD11c, CD14, CD34, CD 45, CD106, CD123, CD133, and HLA-DR markers. This data demonstrates that ELSCs isolated from limbus tissue are not hematopoietic in origin since they are negative for the CD34 and CD45 markers. The remaining CD markers analyzed, CD11c, CD14, CD106, CD123, CD133 and HLA-DR markers, are only known to be expressed in differentiated cells. Therefore, the absence of these markers on the ELSCs demonstrates that these cells are undifferentiated and are not generating cells of differentiated lineages while passaged in culture under the indicated conditions. The expression pattern shown in FIG. 2 also suggests that ELSCs can be maintained in an undifferentiated state, (i.e., maintain "stemness") for at least 20 passages, and that the ELSCs are not hematopoetic in origin.

Interestingly, expression of CD73 and CD105 by ELSCs suggests that these cells are mesenchymal in origin. Therefore, it is hypothesized that ELSCs are derived from the lower stromal cell layer of limbus tissue that contains mesenchymal and fibroblastic cells rather than the upper epithelial cell layer. ELSCs, however, also expressed the CD54 marker, which is known to be an endothelial cell marker. To further understand this finding, the cells were analyzed by RT-PCR for expression of another endothelial marker, the PECAM gene (see FIG. 11).

Pluripotent ELSCs were further assayed for their pluripotency and undifferentiated status through the use of the cellular markers OCT-4, TRA-1-60, TRA-1-80, and Alkaline phosphatase. In order to determine whether these genes were expressed by ELSCs, cultured ELSCs were collected at day 1, 2, 3, 4, 5, 6, 7, 8, 9, 10, 11, 12, 13, 14, 15, 16, 17, and 18 and subjected to gene expression analysis. Strong expression of each of these undifferentiated markers was observed in pluripotent ELSCs. The results of this gene profiling again demonstrate that the pluripotent ELSCs of the present disclosure are undifferentiated stem cells.

2) Molecular Analysis

As found from the experiments and results set forth above, an array of unique markers expressed in ELSCs isolated from limbal tissue have been found. To further characterize the ELSCs, the cells were analyzed by RT-PCR for expression of the following pluripotent stem cell marker genes: Oct-4, Nanog, Rex1, and TDGF1. Expression of Oct-4, Nanog, Rex1, and TDGF1 are down regulated upon differentiation. Expression of the "housekeeping" gene GAPDH, which is ubiquitously expressed in all cells, was also analyzed as a positive control. The identity of the RT-PCR products was confirmed by sequencing. Briefly, total RNA of pluripotent ELSCs was isolated at every passage, for example passage 1, 2, 3, 4, 5, 6, 7, 8, 9, 10, 11, 12, 13, 14, 15, 16, 17, 18, 19, and 20, using the TRIzol method (Gibco-BRL). Next, 1 μg of total RNA treated with RNase-OUT ribonuclease inhibitor (Invitrogen Inc, USA) was used for cDNA synthesis by reverse-transcription using reverse transcriptase (Invitrogen Inc, USA) and oligo dT (Invitrogen Inc, USA) to prime the reaction. For each polymerase chain reaction (PCR) reaction, 2 ul of cDNA was amplified by PCR using Abgene 2×PCR master mix and the appropriate primers. PCR primers were selected to distinguish between cDNA and genomic DNA by using individual primers specific for different exons. The primers used to amply Oct-4, Nanog, Rex1, and TDGF1 cDNAs are set forth below in Table 2. The PCR amplification conditions used in the thermal cycler (ABI Biosystems 9700) to amplify the PCR products were as follows: (1) 94° C., 1 minute; (2) 94° C., 30 seconds; annealing Tm ° C., 45 seconds; 72° C., 1 minute, for 30 cycles of amplification; (3) 72° C., 5 minutes; and (4) final hold at 4° C. until the samples were analyzed.

TABLE 2

| Gene | Primer Sequence | Annealing Temp (° C.) | PCR Product size (bp) |
|---|---|---|---|
| GAPDH | 5'-TGAAGGTCGGAGTCAACGGATTTGGT-3' SEQ ID NO: 1 5'-CATGTGGGCCATGAGGTCCACCAC-3' SEQ ID NO: 2 | 60 | 890 |
| Oct-4 | 5'-CGRGAAGCTGGAGAAGGAGAAGCTG-3' SEQ ID NO: 3 5'-CAAGGGCCGCAGCTTACACATGTTC-3' SEQ ID NO: 4 | 58 | 247 |
| Nanog | 5'-CCTCCTCCATGGATCTGCTTATTCA-3' SEQ ID NO: 5 5'-CAGGTCTTCACCTGTTTGTAGCTGAG-3' SEQ ID NO: 6 | 52 | 262 |
| Rex1 | 5'-GCGTACGCAAATTAAAGTCCAGA-3' SEQ ID NO: 7 5'-CAGCATCCTAAACAGCTCGCAGAAT-3' SEQ ID NO: 8 | 56 | 306 |
| TDGF1 | 5'-GCCCGCTTCTCTTACAGTGTGATT-3' SEQ ID NO: 9 5'-TAGTACGTGCAGACGGTGGTAGTTCT-3' SEQ ID NO: 10 | 55 | 499 |

Figure 3:
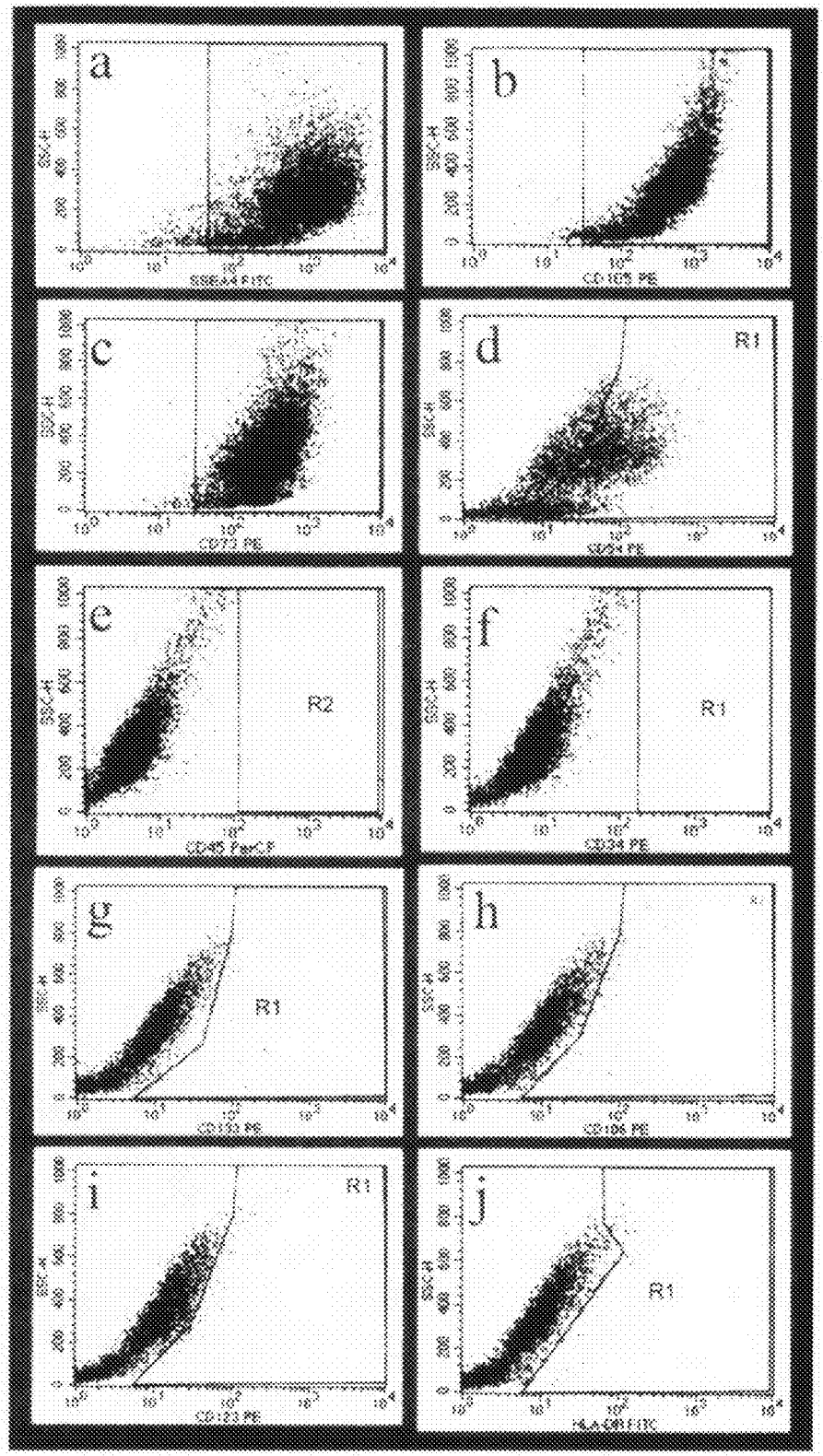
FIG. 3. Gene expression profiling by RT-PCR of the undifferentiated stem cell markers Oct-4, Nanog, Rex1, and TDGF1 after 5, 10, 15, and 20 passages of the isolated ELSCs. GAPDH expression was also analyzed as a positive control. hEF cells were used as a negative control for expression of the undifferentiated stem cell markers, while NTERA (NT) cells were used as a positive control for expression of these markers.

The results of this experiment at the fifth (P5), tenth (P10), fifteenth (P15) and twentieth (P20) passages of the isolated ELSCs are shown in FIG. 3. Expression of Oct-4, Nanog, Rex1 and TDGF1 markers for "stemness" was also analyzed in hEF and NTERA cell lines as negative and positive controls, respectively. The NTERA cell line is an established terato-carcinoma cell line which expresses pluripotent stem cell markers. GAPDH expression appeared to be approximately the same in each sample, indicating that the amount of RNA used for each RT-PCR reaction was quantitatively similar. The same data is reproduced in a tabulated manner in Table 3.

TABLE 3

| Gene | P5 | P10 | P15 | P20 | hEF | NTERA |
|---|---|---|---|---|---|---|
| GAPDH | ++ | ++ | ++ | ++ | ++ | ++ |
| Oct-4 | + | + | ++ | + | + | +++ |
| Nanog | ++ | ++ | ++ | + | − | ++ |
| Rex-1 | ++ | ++ | ++ | ++ | ++ | ++ |
| TDGF1 | ++ | ++ | ++ | + | − | ++ |

Conspicuous expression of all four markers of pluripotent undifferentiated cells was observed in the pluripotent ELSCs at each of the various passages. It appears that expression of at least two of the pluripotency markers, Nanog and TDGF1, gradually decreased, over time. It is possible that this decrease is due to an increased percentage of differentiated cells with the ELSCs as they are passaged in culture, because it is known that expression of these genes is down regulated in differentiated cells. Nevertheless, these results clearly indicate that ELSCs isolated from limbal tissues are pluripotent and have embryonic stem cell-like properties. Although the hEF cell line was a negative control, expression of both Oct-4 and Rex-1 was found in the cell line. Interestingly, there have been reports of undifferentiated stem cell markers being expressed in certain committed cell lines (Abeyta et al., (2004) Hum. Mol. Genet. 13:601-608).

3) Telomerase Activity Analysis

Maintenance of telomerase activity in a pluripotent stem cell line is important for the long-term pluripotency of the cell line. Therefore, telomerase activity of the presently disclosed ELSCs was evaluated over time. ELSCs extracts from passage 5 (P5), 10 (P10), 15 (P15), and 20 (p20) were prepared, and protein concentration in each extract was estimated. The extracts were next evaluated using the telomeric repeat amplification protocol (TRAP), which is an assay designed for highly sensitive qualitative detection of telomerase activity. Telomerase activity was then detected by photometric enzyme immunoassay. Briefly, after estimation of protein concentration, samples were placed in a thermocycler and PCR was performed per the protocol. After PCR amplification, the amplified products were denatures, and detected by ELISA.

Telomerase PCR ELISA was done according to manufacturer's protocol (Roche Molecular Biochemicals), and all proper positive and negative controls provided in the kit were used. The telomerase PCR ELISA allows highly specific amplification of telomerase-mediated elongation products combined with non-radioactive detection following the ELISA protocol. Care was taken during the protocol to remove inhibitors of Taq polymerase, which could result in a false negative result. In the first step of the protocol, telomerase in the extract adds telomeric repeats (TTAGGG SEQ ID NO:11) to the 3' end of biotin-labeled synthetic primer. Next, these elongation products are amplified by PCR using primers that generate PCR products that contain the telomerase-specific six nucleotide increments. An aliquot of the PCR products are denatured and hybridized to a digoxigenin-(DIG)-labeled, telomeric repeat-specific detection probe. The resulting product is immobilized via the biotin labeled primer to a strepatavidin-coated microtiter plate. After detection with an antibody, which is conjugated to peroxidase, telomerase activity is detected by formation of a colored product. High expression of telomerase activity was seen in the extracts of all passages tested, indicating the high proliferative capacity of pluripotent ELSCs.

4) Karyotype Analysis

Figure 4:
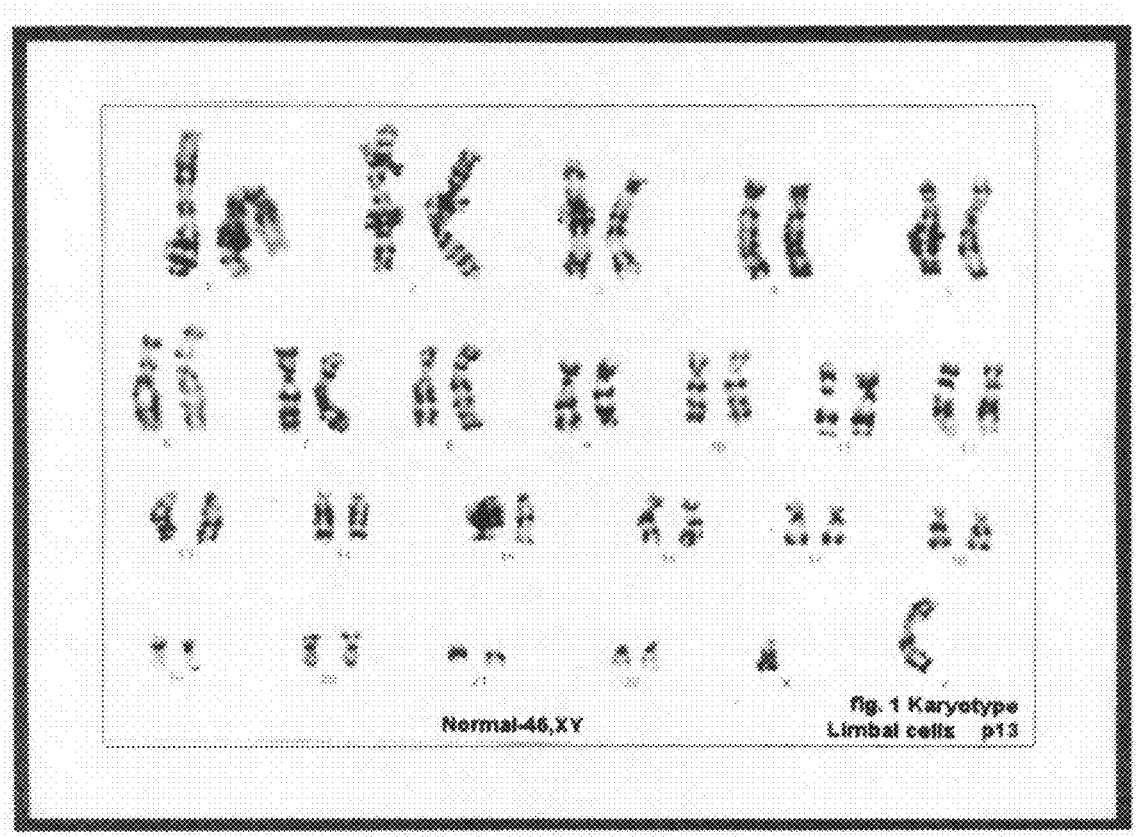
FIG. 4. Karyotyping of ELSCs. ELSCs isolated after 13 passages maintained a normal karyotype (analysis by CYTOVISION software).

To determine whether the pluripotent ELSCs of the present disclosure maintain a normal karyotype in culture, ELSCs were karyotyped using a standard G-banding technique (Genetics Lab., Reliance Life Sciences Pvt. Ltd., Mumbai) and compared to published human karyotypes. The karyotyping was performed using the CYTOVISION software. ELSCs from passage 13 (P13) were karyotyped and found to have 'normal karyotype', that is, the cells at P13 were found to be euploid, all human chromosomes were present, and the chromosomes were not noticeably altered (FIG. 4). ELSCs were also found to have normal karyotypes at passage 20.

Example 3

Differentiation and Analysis of Pluripotent Embryonic-Like Stem Cells

1) Generation of Embryoid-Like Bodies from Pluripotent Embryonic-Like Stem Cells To determine whether the undifferentiated human pluripotent ELSCs could form embryoid-like bodies (ELBs) in culture, the cells were first allowed to proliferate and the cell cultures expanded. Next, the cells were cultured on bacteriological plates having a non-adhesive surface that prevented attachment of the ELSCs, and stimulated differentiation of these cells. Briefly, ELSCs were dissociated by briefly exposing them to a 0.05% trypsin-EDTA solution, and subsequently cultured as a suspension culture in ES cell medium containing DMEM:F-12 or knockout DMEM, supplemented with 10-20% fetal calf serum, cord blood serum, or knockout serum replacement. The media was also supplemented with β-mercaptoethanol, L-glutamine, insulin, human transferrin, sodium selenite, but did not contain bFGF or hLIF. The cells were incubated in suspension culture for about 4 days and the media was changed every other day. The medium was changed by transferring the suspension of aggregates to a centrifuge tube, allowing the aggregates to settle down, aspirating the old medium, replacing it with fresh medium, and returning the aggregates and fresh medium to the culture dish.

Figure 5:
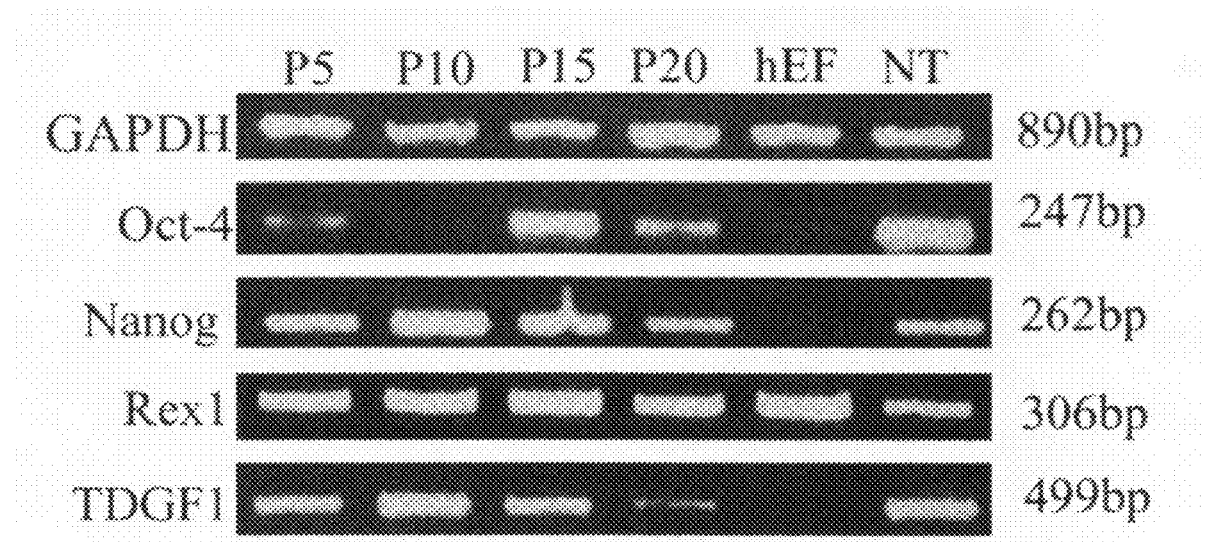
FIG. 5. Phase-contrast micrographs of ELSCs and ELBs (10×): (a) micrograph of passage 15 ELSCs; (b) micrograph of ELBs formed from ELSCs after 4 days of suspension culture; and (c) micrograph demonstrating initiation of differentiation from ELBs formed from ELSCs.

At the end of 4 days, ELBs were collected by spinning down the aggregates at low speed (1000 rpm, 5 minutes) and resuspending the ELBs in the same ES cell medium described above. FIG. 5 shows this differentiation process using phase contrast micrographic pictures (10×). First, FIG. 5(a) shows ELSCs grown in culture after 15 passages. FIG. 5(b) shows ELBS, which formed after culturing ELSCs for 4 days in suspension culture. Finally, FIG. 5(c) shows initiation of differentiation from the ELBs.

To further characterize the process of differentiation from ELSCs to ELBs, the molecular analysis protocol described above in Example 2 was repeated on undifferentiated ELSCs (UD), as well as ELBs after 2 days (EB2), 4 days (EB4), 8 days (EB8), 12 days (EB12), and 14 days (EB14) of differentiation in suspension culture. The cells were analyzed by RT-PCR for expression of the following pluripotent stem cell marker genes: Oct-4, Nanog, Rex1, and TDGF1, the expression of which are down regulated upon differentiation. The primers used to amply Oct-4, Nanog, Rex1, and TDGF1 cDNAs are set forth above in Table 2. In addition, expression of the "housekeeping" gene GAPDH was also analyzed as a positive control. Expression of each of these markers was also analyzed in hEF, which functioned as a negative control. The identity of the RT-PCR products was confirmed by sequencing.

Figure 6:
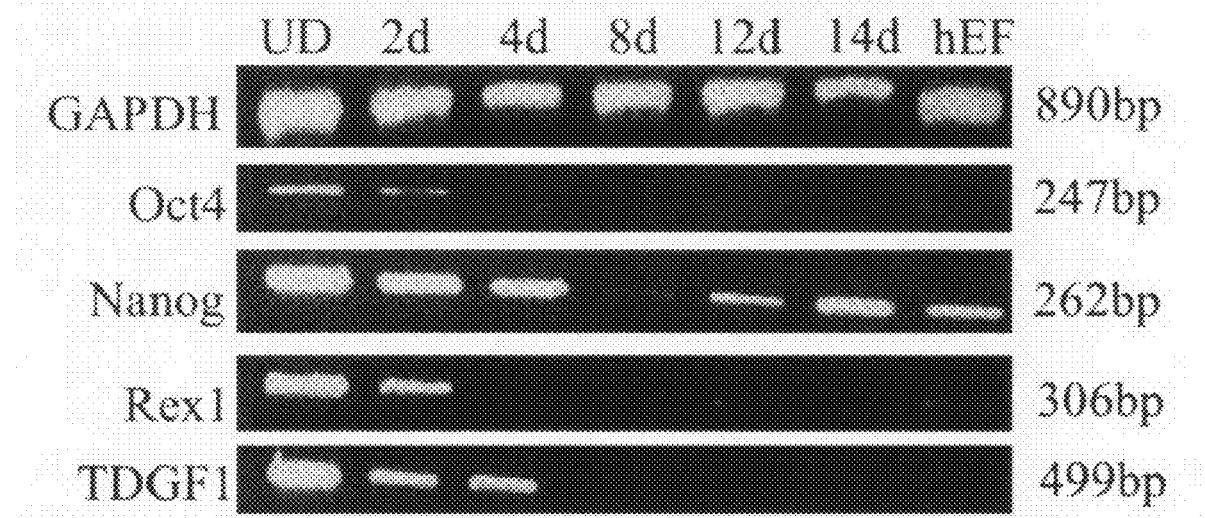
FIG. 6. Gene expression profiling by RT-PCR of the undifferentiated stem cell markers Oct-4, Nanog, Rex1, and TDGF1 in ELSCs (UD) and in ELBs collected on day 2 (2 d), day 4 (4 d), day 8 (8 d), day 12 (12 d), and day 14 (14 d) of ELB formation. GAPDH expression was also analyzed as a positive control. hEF cells were used as a negative control for expression of the undifferentiated stem cell markers.

The results of this experiment are shown in FIG. 6. GAPDH expression appeared to be approximately the same in each sample, indicating that the amount of RNA used for each RT-PCR reaction was quantitatively similar. The same data is reproduced in tabulated form in Table 4.

TABLE 4

| Gene | UD | EB2 | EB4 | EB8 | EB12 | EB14 | hEF |
|---|---|---|---|---|---|---|---|
| GAPDH | ++ | ++ | ++ | ++ | ++ | ++ | ++ |
| Oct-4 | ++ | ++ | − | − | − | − | + |
| Nanog | ++ | ++ | ++ | + | + | + | + |
| Rex-1 | ++ | + | − | − | − | − | + |
| TDGF1 | ++ | + | + | − | − | − | − |

Expression of all four markers was again found in the undifferentiated ELSCs, and expression of each of the genes also appeared to gradually decreased over time as cells in the ELBs differentiated. Although it is surprising that Oct-4, Nanog expression was found in the hEF cell line, there have been reports of undifferentiated stem cell markers being expressed in certain committed cell lines. Although the hEF cell line was a negative control, expression of Oct-4, Nanog, and Rex-1 was found in the cell line. Interestingly, there have been reports of undifferentiated stem cell markers being expressed in certain committed cell lines (Abeyta et al., (2004) Hum. Mol. Genet. 13:601-608).

In addition to examining expression of undifferentiated markers, the same set of cells were analyzed for expression of various genes for ectoderm, mesoderm and endodermal lineages, as well as expression of genes indicating endothelial lineage, stromal cells, and corneal epidermal stem cells. Expression of the following gene markers was analyzed, again by RT-PCR using the protocol outlined in Example 2: Neurofilament Heavy Chain (NFH) and Keratin (ectodermal lineage markers); cardiac-Actin (c-Actin) (mesodermal lineage marker); Alpha-Fetoprotein (AFP) and Albumin (endodermal lineage markers); PECAM (endothelial lineage marker), Keratinocyte Growth Factor (KGF) and Collagen I (stromal cell markers); and p63 (corneal epithelial stem cell marker). The primers used to amply each of these markers are set forth below in Table 5.

TABLE 5

| Gene | Primer sequence | Annealing Temp (° C.) | PCR Product size (bp) |
|---|---|---|---|
| NFH | 5'-TGAACACAGACGCTATGCGCTCAG-3' SEQ ID NO: 12 5'-CACCTTTATGTGAGTGGACACAGAG-3' SEQ ID NO: 13 | 58 | 400 |
| Keratin | 5'-AGGAAATCATCTCAGGAGGAAGGGC-3' SEQ ID NO: 14 5'-AAAGCACAGATCTTCGGGAGCTACC-3' SEQ ID NO: 15 | 56 | 780 |
| c-Actin | 5'-TCTATGAGGGCTACGCTTTG-3' SEQ ID NO: 16 5'-CCTGACTGGAAGGTAGATGG-3' SEQ ID NO: 17 | 50 | 630 |
| AFP | 5'-AGAACCTGTCACAAGCTGTG-3' SEQ ID NO: 18 5'-GACAGCAAGCTGAGGATGTC-3' SEQ ID NO: 19 | 50 | 680 |
| Albumin | 5'-CCTTTGGCACAATGAAGTGGGTAACC-3' SEQ ID NO: 20 5'-CAGCAGTCAGCCATTTCACCATAGG-3' SEQ ID NO: 21 | 58 | 450 |
| PECAM | 5'-GTCATGGCCGTCGAGTA-3' SEQ ID NO: 22 5'-CTCCTCGGCATCTTGCTGAA-3' SEQ ID NO: 23 | 50 | 260 |
| Collagen I | 5'-CCATCCAAACCACTGAAACC-3' SEQ ID NO: 24 5'-TGACGAGACCAAGAACTG-3' SEQ ID NO: 25 | 55 | 600 |
| KGF | 5'-GATACTGACATGGATCCTGCC-3' SEQ ID NO: 26 5'-CACAATTCCAACTGCCACTG-3' SEQ ID NO: 27 | 55 | 300 |
| p63 | 5'-CAGACTCAATTTAGTGAG-3' SEQ ID NO: 28 5'-AGCTCATGGTTGGGGCAC-3' SEQ ID NO: 29 | 48 | 550 |

Figures 7, 8:
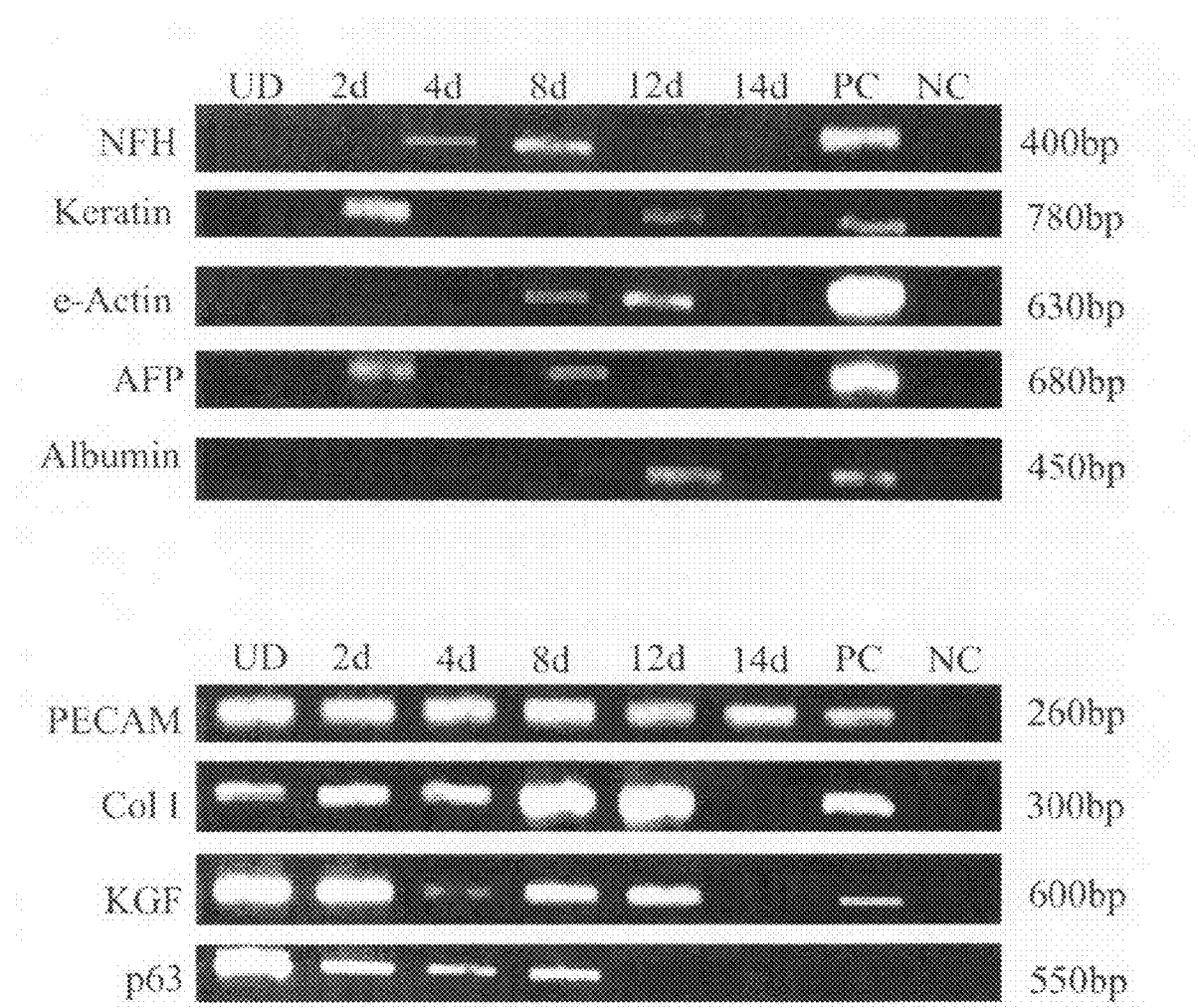
FIG. 7. Gene expression profiling by RT-PCR of lineage markers NFH and Keratin (neuroectoderm lineage markers); c-Actin (mesoderm lineage marker); and AFP and Albumin (endoderm lineage markers) in ELSCs (UD) and in ELBs collected on day 2 (2 d), day 4 (4 d), day 8 (8 d), day 12 (12 d), and day 14 (14 d) of ELB formation. Positive controls (PC) for each marker were as follows: fetal-brain tissue extract for NFH and Keratin; fetal-heart tissue extract for c-Actin; and fetal-liver tissue extract for AFP and Albumin. The negative controls (NC) were (−)RT products.
FIG. 8. Gene expression profiling by RT-PCR of the following markers in ELSCs (UD) and in ELBs collected on day 2 (2 d), day 4 (4 d), day 8 (8 d), day 12 (12 d), and day 14 (14 d) of ELB formation: PECAM, which is an endothelial lineage marker; KGF and Collagen I, which are stromal cell markers; and p63, which is a corneal epithelial stem cell marker. Positive controls (PC) for each marker were as follows: fetal-heart tissue extract for PECAM; hEF cells for KGF and Collagen I; and limbal tissue extract for p63. The negative controls (NC) were (−)RT products.

FIGS. 7 and 8 shows the results of the gene expression pattern of different gene markers in the ELSCs (UD) and in ELBs collected after 2, 4, 8, 12, and 14 days of culture. The positive controls used for each RT-PCR were fetal-brain tissue extract as a neuroectodermal lineage control (for NFH and Keratin), fetal-heart tissue extract as a mesodermal and endothelial lineage control (for c-Actin and PECAM), fetal-liver tissue extract as a endodermal lineage control (for AFP and Albumin), hEF cells as a stromal cell control (for Collagen I and KGF), and limbal tissue extract as a corneal epidermal stem cell control (for p63), while the negative control was (−)RT product. The same data as shown in FIGS. 7 and 8 are reproduced in a tabulated manner in Table 6.

TABLE 6

| Gene | UD | EB2 | EB4 | EB8 | EB12 | EB14 | PC | NC |
|---|---|---|---|---|---|---|---|---|
| NFH | − | − | + | ++ | − | − | ++ | − |
| Keratin | − | ++ | − | − | ++ | − | ++ | − |
| c-Actin | − | − | − | + | ++ | − | +++ | − |
| AFP | − | ++ | − | + | − | − | ++ | − |
| Albumin | − | − | − | + | ++ | − | ++ | − |
| PECAM | ++ | ++ | ++ | ++ | ++ | ++ | ++ | − |
| Col I | + | + | + | ++ | ++ | − | ++ | − |
| KGF | ++ | ++ | + | ++ | ++ | − | + | − |
| p63 | ++ | + | + | + | − | − | − | − |

Expression of Keratin, KGF, Collagen-I, and P-63 in the ELSCs and ELBs indicates that the cells are derived from limbal tissue. Keratin is an early ectodermal lineage marker, while expression of KGF and Collagen-I at nearly all stages is expected because they are both markers for fibroblastic cells, and ELSCs are isolated from the stromal layer. It is unclear why expression of Collagen-I appears to be upregulated at day 8 and 12 of ELB formation, but is not present at day 14 of ELB formation. P-63 expression was found in the population of undifferentiated ELSCs, indicating that these cells also contain a population of corneal limbal stem cells. P-63 expression decreased as the ELSCs differentiate during ELB formation.

The lineage markers NFH, c-Actin, AFP, and Albumin do not appear to be expressed in the ELSCs, but are expressed at various stages of differentiation in the ELBs. NFH, which is an early neuro-ectodermal marker, is not expressed in undifferentiated ELSCs, but is expressed at day 4 and 8 of ELB formation. NFH was not expressed in later stages of ELB formation, however, because expression of this marker is downregulated upon maturation of neuronal cells. c-Actin, which is a mesodermal lineage marker, is highly expressed by day 12 of ELB formation. AFP, which is an early mesendodermal marker, is highly expressed at day 2 of ELB formation, but is gradually downregulated as the ELBs differentiate. Expression of Albumin, which is a mature hepatic cell marker, is gradually upregulated as ELBs differentiate. PECAM is expected to be expressed at all stages of embryonic development, and is closely correlated with the pluripotency of reported cells (Furusawa et al., (2004) Biol. Reprod. 70:1452-57). The differential expression of appropriate lineage markers in ELBs at various stages of differentiation indicates the ability of ELSCs to differentiate into cells of all three lineages.

2) Differentiation of Pluripotent Embryonic-Like Stem Cells into Neurons

To determine whether ELSCs of the present disclosure can differentiate into neurons, ELBs derived from ELSCs were cultured for approximately 4-10 days in an appropriate medium and plated directly onto a suitable substrate with an extracellular matrix component such as polyornithine, laminin, or fibronectin. The ELBs were cultured in a suitable nutrient medium adapted to promote differentiation of the cells into neuroprogenitor cells. Then the cells were further cultured under conditions that encouraged differentiation and maturation into specific neuronal phenotypes, including GABAergic and dopaminergic neurons.

Derivation of GABAergic Neurons

ELBs were cultured in serum-free neuronal induction medium composed of basal medium DMEM:F12 along with additives that help sustain cultures of neural cells, for example N2 (1-15%) and B27 (1-20%). The medium was also supplemented with one or more growth factors selected from Retinoic acid (20-80 ng/ml), GDNF (1-10 µg/ml), Ara-C (10-50 ng/ml), and Neurotrophin-3 (5-20 µg/ml). The cells were grown for 6 days, which resulted in the differentiation of neuroprogenitor cells.

Next, the neuroprogenitor cells were grown in a neural differentiation medium containing Neurobasal medium supplemented with N2 (1-15%), B27 (1-20%), and growth factors including insulin (5-20 µg/ml), Transferrin (4-10 µg/ml), FGF-8 (50-200 ng/ml), and Ara-C (10-50 ng/ml) for 12 days with the media being change every second day. To generate cells having a mature neuronal-like morphology, the cells were grown in neural differentiation medium that was supplemented with other neuronal growth factors such as neutrotrophin-3 and GDNF. In particular, Neurotrophin-3 (5-20 µg/ml) and GDNF (1-10 µg/ml) were added to the differentiation medium on day 6 to day 12 of differentiation.

Derivation of Dopaminergic Neurons

The ELBs were cultured in serum-free defined medium composed of DMEM:F12 supplemented with N2 (1-15%) and B27 (1-20%), along with one or more antioxidants, such as DMSO (1-10%), Butylated hydroxyanisole (50-400 µM), and forskolin (5-20 µM), for initiation of neuronal induction. After 4-7 days of culture, one or a combination of growth factors such as Retinoic acid (20-80 ng/ml), GDNF (1-10 µg/ml), Shh (50-200 ng/ml), FGF-8 (50-200 ng/ml), or bFGF (10-50 ng/ml) were added to the medium to facilitate neuronal differentiation. The cells were grown in this medium for an additional 7-10 days. Changes in cell morphology of the cultured cells were observed within 48 hours. The percentage of responsive cells increased progressively with incubation under antioxidant and serum-free conditions. The neuroprogenitor cells were next grown in neuronal maturation media containing Neurobasal medium supplemented with N2 (1-15%), B27 (1-20%), GDNF (1-10 µg/ml), Retinoic acid (20-80 ng/ml), db-cAMP (10-200 µM), and IL-1b (1-5 µg/ml). Under these culture conditions, about 30-40% of the cells extended neurite processes and stained positive for β-tubulin, which evidenced their ability to form neurons. The growth factors present in the neuronal induction medium contribute to the overall increase in percentage of neuronal cells, and further induce these precursor cells to adopt the dopaminergic phenotype.

Characterization of Differentiated Neurons

The differentiated neuronal cell types generated according to the above protocols were evaluated both by the overall morphology of the cells, as well as the phenotypes identified by immunofluorescence. Immunofluorescence analysis was carried out at day 12 and day 25 of differentiation of GABAergic and dopaminergic neurons, respectively. First, the isolated cells were grown on 2-well chamber slides pre-coated with extracellular matrices, rinsed with PBS, and fixed for 10 minutes with 4% paraformaledyde at room temperature. Next, the cells were permeabilized with 0.2% Triton X-100 in PBS for 5 minutes, blocked with 1% bovine serum albumin (BSA)/PBS for 2 hours, and incubated with a primary antibody (antibody dilutions were made in 1% BSA/Tris-buffered saline) overnight at 4° C.

Figure 9:
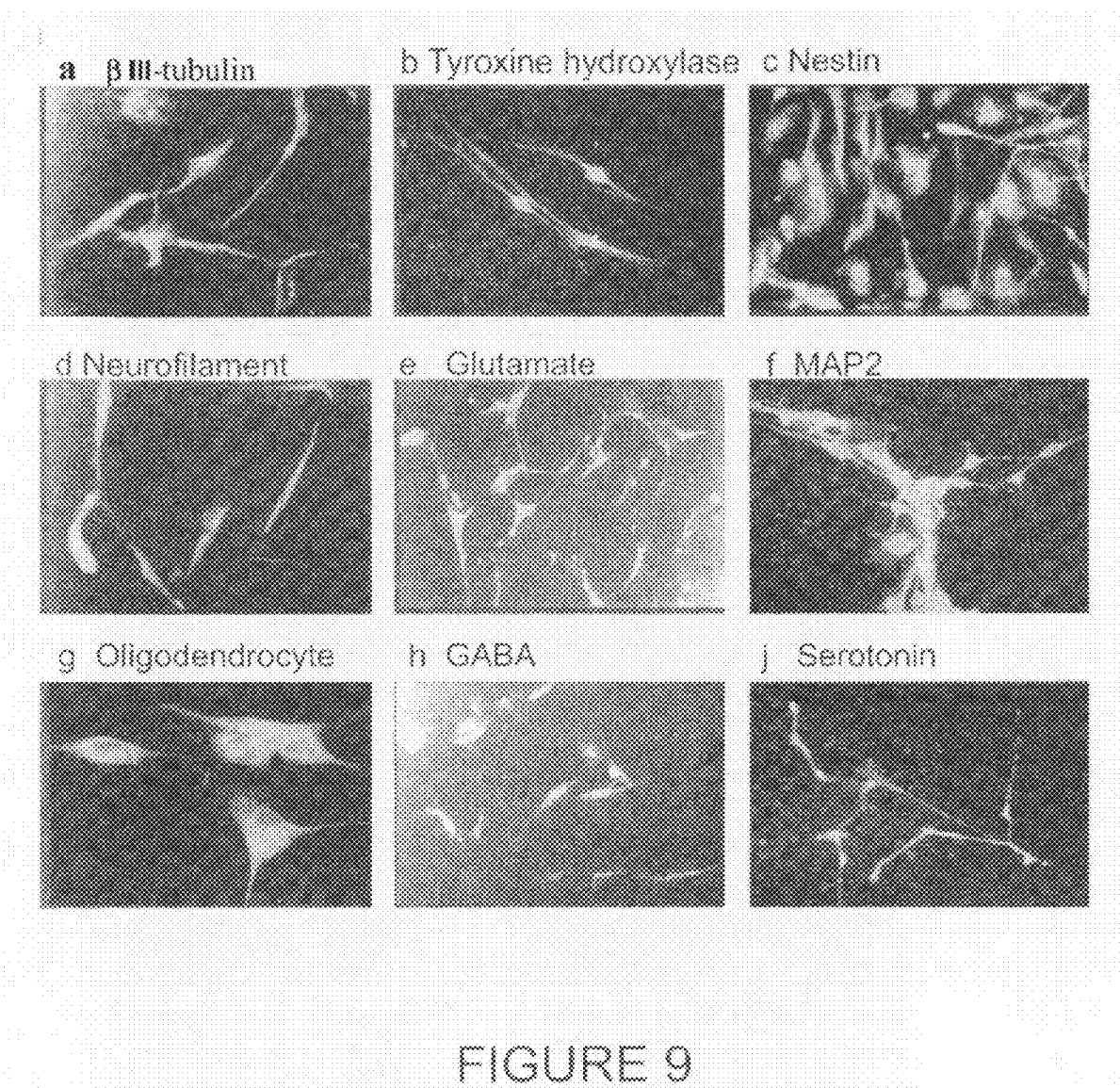
FIG. 9. Immunofluorescence assays of neuronal cells differentiated from ELSCs through the formation of ELBs (10×). Immunological characterization of neuronal cells differentiated from ELSCs showed positive immunofluorescence for the neuronal markers β-tubulin III, Neurofilament, O4, Glutamate, GABA, Tyrosine hydroxylase, Serotonin, Nestin.

The cells were stained with the following primary antibodies: early neuronal marker β-tubulin III (1:500); late neuronal marker Microtubule associated protein 2 (MAP-2) (1:200); gamma aminobutyric acid (GABA) (1:200); Glutamate (1:500); Nestin (1:50); Neurofilament (1:500); Tyrosine hydroxylase (TH) (1:800); Serotonin (1:500) and Oligodendrocyte (1:500). All primary antibodies were obtained from Chemicon Inc., USA. Next, the cells were incubated with the appropriate FITC-labeled secondary antibody. After each step, the cells were washed three times with PBS. The chamber slides were observed under a fluorescence microscope to evaluate the immunopositive areas. This immunofluorescence analysis, as shown in FIG. 9, demonstrated that many of the differentiated cells were immunoreactive to the neuron specific markers MAP-2, β-tubulin III, and Neurofilament, as well as the phenotype specific markers TH (marker for dopaminergic neurons), GABA (marker for GABAergic neurons), Glutamate (marker for glutamatergic neurons), and Serotonin (marker for serotonergic neurons). Only a few cells expressed the non-neuronal marker O4, which is present in Oligodendrocytes (glial cells).

ELSCs and differentiated neuronal cell types generated above were also analyzed for expression of β-tubulin and Tyrosine hydroxylase (TH) by RT-PCR as previously described above using the following primers:

TABLE 7

| Gene | Primer sequence | Annealing Temp (° C.) | PCR Product size (bp) |
|---|---|---|---|
| β-tubulin | 5'-GGAACATAGCCGTAAACTGC-3' SEQ ID NO: 30<br>5'-AGTTCACTGYGCCTGAACTTACC-3' SEQ ID NO: 31 | 60 | 317 |
| TH | 5'-TGTCAGAGCAGCCCGAGGTC-3' SEQ ID NO: 32<br>5'-CCAAGAGCAGCCCATCAAAG-3' SEQ ID NO: 33 | 63 | 417 |

Figure 11:
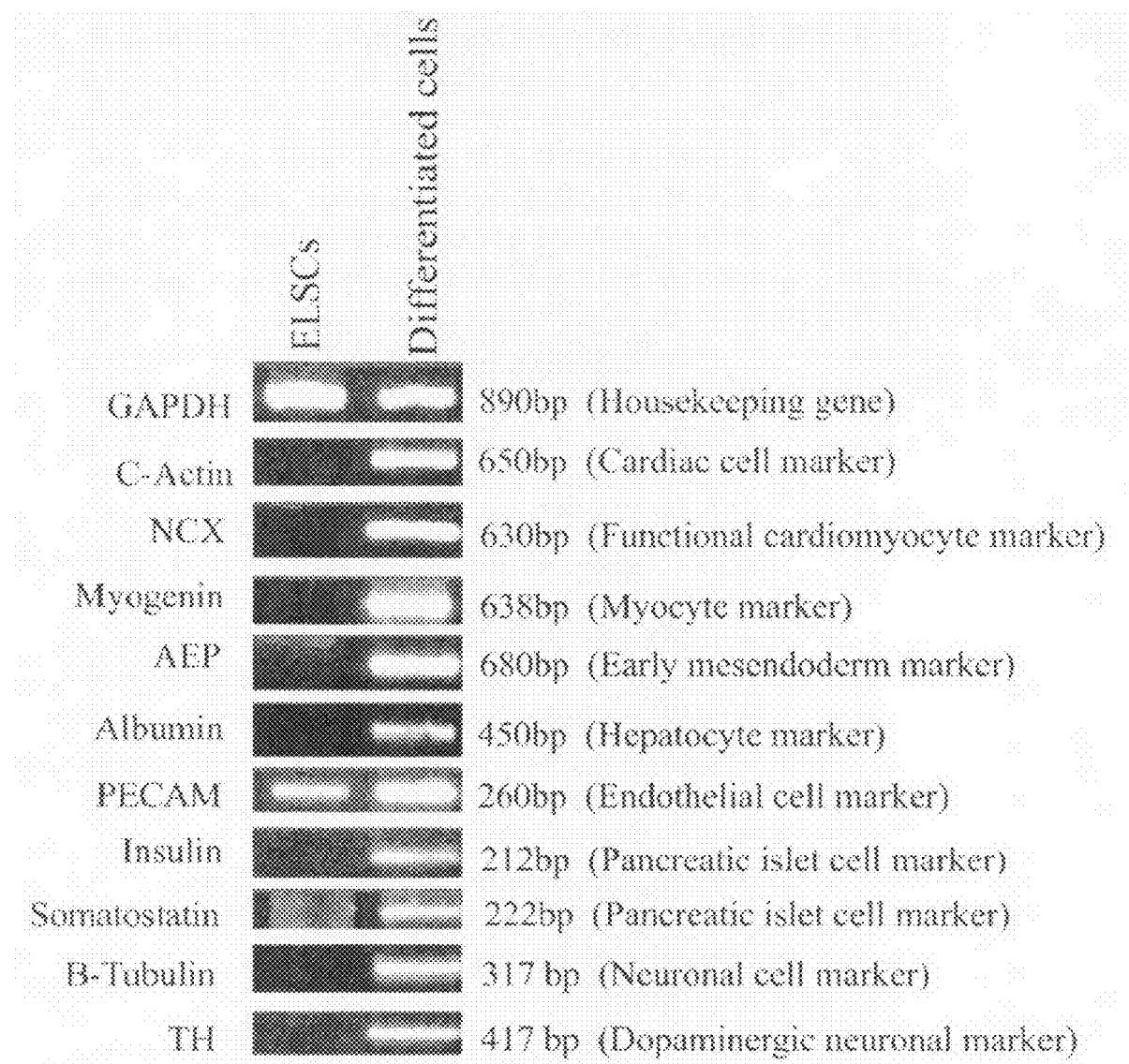
FIG. 11. Gene expression profiling of differentiated cells of various lineages derived from ELSCs by RT-PCR. Positive expression of the following markers was found: c-Actin (cardiac cell marker); NCS (functional cardiomyocyte marker); Myogenin (myocyte marker); Alpha-Fetoprotein (AFP) (early mesendoderm marker); Albumin (hepatocyte marker); PECAM (endothelial cell marker); Insulin (pancreatic islet cell marker); Somatostatin (pancreatic islet cell marker); β-tubulin (neuronal cell marker); and Tyrosine hydroxylase (TH) (dopaminergic neuronal marker). GAPDH expression was also analyzed as a positive control.

Expression of c-Actin and NCX is indicative of adult cardiomyocyte formation. The PCR primers used to amplify the cDNAs were specific for exon sequence of each gene, thereby allowing amplification of cDNA only, and not genomic DNA encoding the genes. FIG. 11 shows the results of RT-PCR analysis for the expression of cardiomyocyte specific markers in ELSCs and differentiated cardiomyocytes derived therefrom. As shown, both c-Actin and NCX are expressed in the differentiated cardiomyoctyes, and not in the undifferentiated ELSCs. The housekeeping gene GAPDH was used as a positive control as previously described.

Functional Characterization of Dopaminergic Neurons by RP-HPLC

The functional capacity of ELSC-derived dopaminergic neurons to produce dopamine was evaluated by directly measuring the extracellular dopamine levels using Reverse Phase HPLC (RP-HPLC). The concentration of dopamine detected in culture supernatant was determined by comparison with a standard solution of dopamine injected into the column immediately before and after each analysis. Approximately $5 \times 10^6$ cells were trypsinized and pelleted by centrifugation. The cells were then sonicated in cold 1N perchloric acid with antioxidants (0.2 g/l sodium metabisulphite), and centrifuged at 15,000 rpm/min for 20 minutes at 4° C. Next, the culture supernatant was immediately stabilized with 7.5% orthophosphoric acid and sodium metabisulphite, and stored at −70° C. for subsequent determination of the extracellular dopamine concentration by RP-HPLC. Dopamine levels in the culture supernatant (48 hours after the last medium change) at day 25 of differentiation was approximately 70 µg/ml.

Differentiated neuronal cells derived from ELSCs (e.g., glutamatergic, GABAergic, serotonergic, and dopaminergic neurons, as well as oligodendrocytes) may be utilized for various applications, such as therapeutic application, as well as in vitro and in vivo assessment and screening of various compounds such as small molecule drugs for their effects on neuronal cells. The neuronal cells may be used, for example, to treat or prevent various neurological or neurodegenerative disorders or diseases including but limited to Parkinson's disease, Alzheimer's disease, Huntington's disease, Lewy body dementia, multiple sclerosis, cerebellar ataxia, progressive supranuclear palsy, spinal cord injury, amyotrophic lateral sclerosis (ALS), epilepsy, stroke, ischemia, injury or trauma to the nervous system, neurotoxic injury, and the like, in which neuronal cells, neurons, or glial cells are injured or die in the central nervous system or spinal cord. Additionally, the neuronal cells derived from pluripotent ELSCs can also used to treat neurological disorders associated with cognition and psychology including but not limited to anxiety disorders, mood disorders, obsessive-compulsive disorders (OCD), personality disorders, attention deficit disorder (ADD), attention deficit hyperactivity disorder (ADHD), and schizophrenia.

3) Differentiation of Pluripotent Embryonic-Like Stem Cells into Osteoblasts

To determine whether ELSCs of the present disclosure could differentiate into osteoblasts, ELBs derived from ELSCs were cultured for approximately 4-10 days in an appropriate medium and plated directly onto a suitable substrate with an extracellular matrix component such as poly-ornithine, laminin, or fibronectin. The ELBs were cultured in a suitable nutrient medium adapted to promote differentiation of the cells into osteoblasts. For example, the ELBs were cultured in DMEM supplemented with 10-15% fetal bovine serum in the presence dexamethasone (10-100 nM), glycerophosphate, (1-10 mM), ascorbic acid 2 phosphate (0.1-0.5 mM), bone morphogenic protein 2 (BMP2) (1-10 ng/ml), and hydrocortisone (0.05-0.1 µM). The cells were cultured for approximately 28 days.

Figure 10:
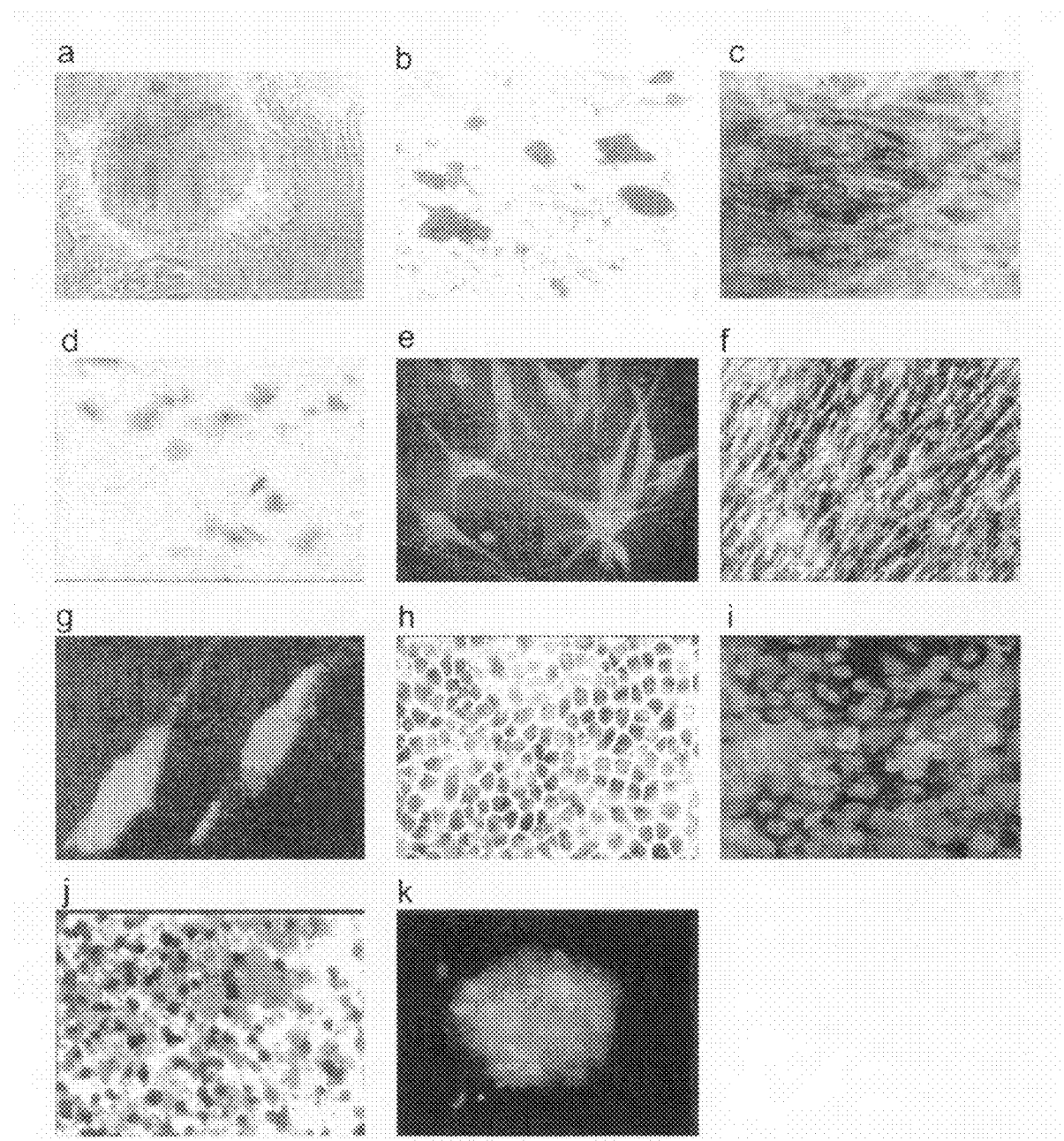
FIG. 10. Cellular and functional characterization of various differentiated cell-types from ELSCs through the formation of ELBs: (a) initiation of differentiation from ELBs; (b) Von Kossa staining of osteoblasts; (c) Alcian Blue staining of chondrocytes; (d) Oil Red-O staining of adipocytes; (e) immunofluorescence of myocytes with anti-myogenin antibody; (f) phase contrast micrograph of beating cardiomyocytes (10×); (g) immunofluorescence of cardiomyocytes with anti-cTnT antibody; (h) phase contrast micrograph of mature hepatocytes derived from ELSCs; (i) immunofluorescence of hepatocytes with anti-albumin antibody; (j) PAS staining of mature hepatocytes showing insoluble glycogen deposits; (k) immunofluorescence of pancreatic beta-islet cells with anti-PDX-1 antibody.

The cells isolated from the above differentiation protocol were analyzed to confirm the presence of osteoblasts in the culture. First, the differentiated cells were analyzed for calcium deposits, which are indicative of osteoblasts, by Von Kossa staining (Pittenger et al., (1999) Science 284:143-147, incorporated herein by reference). FIG. 10(b) shows Von Kossa staining of abundant calcium deposits (deep brown bodies) in osteoblasts derived from ELSCs after 17 days of differentiation culture.

4) Differentiation of Pluripotent Embryonic-Like Stem Cells into Chondrocytes

To determine whether ELSCs of the present disclosure could differentiate into chondrocytes, ELBs derived from ELSCs were cultured for approximately 4-10 days in an appropriate medium and plated directly onto a suitable substrate with an extracellular matrix component such as poly-ornithine, laminin, or fibronectin. The ELBs were cultured in a suitable nutrient medium adapted to promote differentiation of the cells into chondrocytes. For example, the ELBs were cultured in DMEM supplemented with 10-15% knockout serum and in the presence of TGF beta-3 (10-100 ng/ml), ascorbic acid (0.01-0.05 mM), 1×ITS, and sodium pyruvate (1-5 mM). The cells were cultured for approximately 21 days.

The cells isolated from the above differentiation protocol were analyzed to confirm the presence of chondrocytes in the culture. The differentiated cells were analyzed for the presence of glycogen deposits, which are indicative of chondrocytes, by staining with Alcian Blue (Pittenger et al., (1999) Science 284:143-147). FIG. 10(c) shows Alcian Blue staining of sulfated proteoglycan deposits in chondrocytes derived from ELSCs after 17 days of differentiation culture.

5) Differentiation of Pluripotent Embryonic-Like Stem Cells into Adipocytes

To determine whether ELSCs of the present disclosure could differentiate into adipocytes, ELBs derived from ELSCs were cultured for approximately 4-10 days in an appropriate medium and plated directly onto a suitable substrate with an extracellular matrix component such as poly-ornithine, laminin, or fibronectin. The ELBs were cultured in a suitable nutrient medium adapted to promote differentiation of the cells into adipocytes. For example, the ELBs were cultured in DMEM supplemented with 10-15% knockout serum and in the presence of dexamethasone (1 µM-100 mM), isobutylmethylxanthine (IBMX) (10-50 ng/ml), insulin (10-20 ng/ml), indomethac (2-20 mM), and insulin-like growth factor (IGF) (10-100 ng/ml). The cells were cultured for approximately 14 days.

The cells isolated from the above differentiation protocol were analyzed to confirm the presence of adipocytes in the culture. The differentiated cells were analyzed for the presence of cytoplasmic lipid droplets, which are indicative of adipocytes, by staining with Oil Red-O (Pittenger et al., (1999) Science 284:143-147). FIG. 10(d) shows Oil Red-O staining of abundant deposits of lipid droplets in adipocytes derived from ELSCs after 12 days of differentiation culture.

6) Differentiation of Pluripotent Embryonic-Like Stem Cells into Hepatocytes

To determine whether ELSCs of the present disclosure could differentiate into hepatocytes, ELBs derived from ELSCs were cultured for approximately 4-10 days in an appropriate medium and plated directly onto a suitable substrate with an extracellular matrix component such as poly-ornithine, laminin, or fibronectin. The ELBs were cultured in a suitable nutrient medium adapted to promote differentiation of the cells into hepatocytes. For example, the ELBs were cultured in DMEM supplemented with 10-15% knockout serum, EGF (10-100 ηg/ml), hepatocyte growth factor (HGF) (5-50 µg/ml), bFGF (5-20 ng/ml), FGF-4 (5-50 µg/ml), IL-6 (10-100 µg/ml), acidic FGF (50-100 ng/ml), human oncostatin (10-50 ng/ml), insulin-transferrin-selenious acid (ITS) (1×), dexamethasone (10-100 ηM), sodium butyrate (1-5 mM), DMSO (0.5-1%), and 5-azacytidine (1-10 µM). The growth factors were added together or at different time points to the cultured cells as early growth factors, mid-stage growth factors, or late stage growth factors. The cells were cultured for 20 days.

The morphology of the differentiated hepatocytes generated above was examined by phase contrast microscopy (FIG. 10(h)) and by hematoxylin—eosin staining. The hepatocytes were also analyzed for gene expression using RT-PCR, immunological characterization by immunofluorescence using anti-albumin antibody, and functional characterization by evidence of stored glycogen in the cells as detected by periodic-acid-Schiff's staining (PAS). These analyses were carried out at the end of differentiated stage, preferably 20 days after hepatocyte differentiation as disclosed in the above protocol. FIG. 10(d) shows insoluble glycogen deposits in mature hepatocytes by PAS staining. Moreover, as a continuation of extensive functional characterization of ELSC-derived hepatocytes, the potential of these hepatocytes as a prospective drug screening tool is being confirmed by evaluating the hepatocytes for glucose-6-phosphatase activity, uptake of LDL, and albumin production, as well as analyzing cytochrome p450 and Urea assays of the differentiated cells.

To prepare the differentiated hepatocyte cells for immunofluorescence analysis, 21-day old hepatocytes (oval-shaped) were first fixed with paraformaldehyde (Sigma-Aldrich) for 20 minutes. Next, the hepatocytes were rinsed once with PBS at room temperature (RT), and either stored at 4° C. or directly permeabilized with 0.2% Triton X-100 for 5 minutes at RT. After aspirating the fixative, the hepatocytes were washed three times (5 minutes each) with PBS, and blocked with PBS containing 1% BSA for 1 hour at RT. After 2 more washes with 1×PBS, the hepatocytes were incubated with a primary antibody solution diluted in 1×PBS-1% BSA overnight at RT. The primary antibody used was to cytokeratin 18 (CK18), 1:200 (Chemicon, Inc, USA). CK18 is expressed on hepatocyte plasma membrane surface (Wells et al., (1997) J. Biol. Chem. 272:28574-581). The next day, the hepatocytes were washed with 1×PBS three times (10 minutes each) on a rocker, and incubated with a secondary antibody dilution containing a fluorescent label FITC in 1×PBS-1% BSA at RT for 1 hour on a rocker. After three washes with PBS (5 minutes each), the hepatocytes were exposed to 1 mg/ml DAPI solution. The hepatocytes were washed twice with 1×PBS (5 minutes each), and mounted on slides with DPX mountant. FIG. 10(e) shows that hepatocytes differentiated from ELSCs stain positive for the anti-CK18 antibody.

Hepatocytes differentiated from ELSCs were also analyzed for expression of AFP and Albumin by RT-PCR as described above. FIG. 11 shows expression of AFP and Albumin that is indicative of both early and mature hepatocyte formation.

7) Differentiation of Pluripotent Embryonic-Like Stem Cells into Pancreatic Beta-Islet Cells To determine whether ELSCs of the present disclosure could differentiate into pancreatic beta-islet cells, ELBs derived from ELSCs were cultured for approximately 4-10 days in an appropriate medium and plated directly onto a suitable substrate with an extracellular matrix component such as polyornithine, laminin, or fibronectin. The ELBs were cultured in a suitable nutrient medium adapted to promote differentiation of the cells into pancreatic beta-islet cells. For example, the ELBs were cultured in DMEM supplemented with 10-15% knockout serum and in the presence of N2 supplement (1%), B27 supplement (2%), forskolin (10 µM), and cyclopamine (10 µM). The cells were cultured for approximately 12 days.

The cells isolated from the above differentiation protocol were analyzed to confirm the presence of pancreatic beta-islet cells in the culture using immunofluorescence analysis, as described above for differentiated hepatocytes. The differentiated cells were analyzed using immunofluorescence for staining with an anti-PDX-1 antibody, which is indicative of beta-islet cells. Insulin-promoting factor-1 (PDX-1) is a transcription factor expressed by beta-islet cells of the pancreas. FIG. 10(k) shows positive immunofluorescence in beta-islet cells derived from ELSCs after staining with anti-PDX-1 antibody. The beta-islet cells were also analyzed for gene expression of insulin and somatostatin using RT-PCR as previously described using the following primers:

TABLE 8

| Gene | Primer sequence | Annealing Temp (° C.) | PCR Product size (bp) |
|---|---|---|---|
| Insulin | 5'-CCCTGCTGGCCCTGCTCTT-3' SEQ ID NO: 34 5'-AGGTCTGAAGGTCACCTGCT-3' SEQ ID NO: 35 | 58 | 212 |
| Somatostatin | 5'-GTTTCTGCAGAAGTCTCTGG-3' SEQ ID NO: 36 5'-AGTTCTTGCAGCCAGCTTTG-3' SEQ ID NO: 37 | 56 | 222 |

FIG. 11 shows expression of insulin and somatostatin by differentiated cells, which are indicative of beta-islet cells.

8) Differentiation of Pluripotent Embryonic-Like Stem Cells into Cardiomyocytes

To determine whether ELSCs of the present disclosure could differentiate into cardiomyocytes, ELBs derived from ELSCs were cultured for approximately 4-10 days in an appropriate medium and plated directly onto a suitable substrate with an extracellular matrix component such as polyornithine, laminin, or fibronectin. The ELBs were cultured in a suitable nutrient medium adapted to promote differentiation of the cells into cardiomyocytes. For example, the ELBs were cultured in DMEM/F-12 (1:1) supplemented with 15% knockout serum and 100 mM L-glutamine in the presence of EGF (50 ηM), TGF beta-3 (10 µg/ml), bFGF (50 ηg/ml), PDGF-BB (50 µg/ml), and ITS (1×). A well known cardiomyocyte inducing factor for human ES cells, 5-Azadeoxycitidine (5-10 ηM), was not found to be useful for differentiating ELSCs into cardiomyocytes. The cardiotropic factors were added together or at different time points to the differentiation media as early growth factors, mid-stage growth factors, or late stage growth factors. The cells were cultured for approximately 21 days, and were carefully monitored for contracting embryoid-like bodies (i.e., beating cardiac cells), for example through a phase contrast microscope.

The cells isolated from the above differentiation protocol were evaluated morphologically to confirm the presence of ELSC-derived cardiomyoctyes, as shown in FIG. 10(f). In addition, the ELSC-derived cardiomyocytes were analyzed for expression of cardiac troponin T (cTnT), which is a marker characteristic of cardiomyocytes, using the anti-cTnT antibody (Santacruz, USA). FIG. 10(g) shows that these cells are recognized by anti-cTnT antibody, which is indicative of cardiomyocytes. Both ELSCs and cardiomyocytes differentiated from ELSCs were analyzed for expression of c-Actin and Na—Ca exchanger (NCX) by RT-PCR as previously described above using the following primers:

TABLE 9

| Gene | Primer sequence | Annealing Temp (° C.) | PCR Product size (bp) |
|---|---|---|---|
| c-Actin | 5'-TCTATGAGGGCTACGCTTTG-3' SEQ ID NO: 38 5'-CCTGACTGGAAGGTAGATGG-3' SEQ ID NO: 39 | 50 | 630 |
| NCX | 5'-ATGCTTCGATTAAGTCTCCCAC-3' SEQ ID NO: 40 | 50 | 630 |

TABLE 9-continued

| Gene | Primer sequence | Anneal-ing Temp (° C.) | PCR Product size (bp) |
|---|---|---|---|
| | 5'-TAAAGCCAGGTATAGGCAAAGA-3'<br>SEQ ID NO: 41 | | |

Expression of c-Actin and NCX is indicative of adult cardiomyocyte formation. The PCR primers used to amplify the cDNAs were specific for exon sequence of each gene, thereby allowing amplification of cDNA only, and not genomic DNA encoding the genes. FIG. 11 shows the results of RT-PCR analysis for the expression of cardiomyocyte specific markers in ELSCs and differentiated cardiomyocytes derived therefrom. As shown, both c-Actin and NCX are expressed in the differentiated cardiomyoctyes, and not in the undifferentiated ELSCs. Additionally, the potential of these ELSC-derived cardiomyocytes in cell therapy for cardiac diseases is being assessed by extensive functional characterization of the cardiomyocytes by electrophysiology, as well as testing using in vivo animal models.

9) Differentiation of Pluripotent Embryonic-Like Stem Cells into Myocytes

To determine whether ELSCs of the present disclosure could differentiate into myocytes, ELBs derived from ELSCs were cultured for approximately 4-10 days in an appropriate medium and plated directly onto a suitable substrate with an extracellular matrix component such as polyornithine, laminin, or fibronectin. The ELBs were cultured in a suitable nutrient medium adapted to promote differentiation of the cells into myocytes. For example, the ELBs were cultured in DMEM supplemented with 10-15% knockout serum and in the presence of 5-Azacytidine (5-10 μM) and PDGF-BB (10-50 ng/ml). The cells were cultured for approximately 12 days.

The cells isolated from the above differentiation protocol were analyzed for expression of Myogenin, which is a member of the gene family encoding muscle-specific basic-helix-loop-helix transcription factors that is activated in myoblasts at the onset of differentiation. Antibodies to Myogenin (Santacruz, USA) were used to confirm the presence of myocytes in the culture. FIG. 10(e) shows that these cells are recognized by anti-Myogenin antibody. Both ELSCs and cells differentiated from ELSCs were also analyzed for expression of Myogenin by RT-PCR as previously described above. FIG. 11 shows expression of Myogenin in differentiated cells, which is indicative of myocytes.

10) Differentiation of Pluripotent Embryonic-Like Stem Cells into Endothelial Cells To determine whether ELSCs of the present disclosure could differentiate into endothelial cells, ELBs derived from ELSCs were cultured for approximately 4-10 days in an appropriate medium and plated directly onto a suitable substrate with an extracellular matrix component such as polyornithine, laminin, or fibronectin. The ELBs were cultured in a suitable nutrient medium adapted to promote differentiation of the cells into endothelial cells. For example, the ELBs were cultured in DMEM supplemented with 10-15% knockout serum and in the presence of VEGF (20 ng/ml), bFGF (50 ng/ml), and BMP-4 (1-10 ng/ml). The cells were cultured for approximately 21 days.

Both ELSCs and endothelial cells differentiated from ELSCs were analyzed for expression of PECAM by RT-PCR as previously described above. FIG. 11 shows expression of PECAM in both ELSCs and differentiated cells, which is indicative of endothelial cells.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are chemically or physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of isolating a population of human pluripotent embryonic-like stem cells (ELSCs), comprising the steps of:
   (a) isolating human corneal limbal tissue from a donor;
   (b) removing the epithelial layer of the human corneal limbal tissue,
   (c) culturing the human corneal limbal tissue on an extracellular matrix to expand corneal limbal cells in culture;
   (d) dissociating the cultured corneal limbal cells from the extracellular matrix; and
   (e) isolating a population of human pluripotent ELSCs from the cultured corneal limbal cells by sorting the corneal limbal cells to select for an undifferentiated cell-specific surface marker selected from the group consisting of SSEA-4 and SSEA-3,
wherein the isolated pluripotent ELSCs are capable of forming embryoid-like bodies when placed in suspension culture and the pluripotent ELSCs remain substantially undifferentiated after 20 passages in culture.

2. The method of claim 1, wherein the extracellular matrix is a basement membrane.

3. The method of claim 1, wherein the extracellular matrix is mammalian amniotic membrane.

4. The method of claim 1, wherein the corneal limbal tissue is cultured in culture media supplemented with one or more soluble factors selected from the group consisting of dimethyl sulphoxide, recombinant human epidermal growth factor, insulin, sodium selenite, transferrin, basic fibroblast growth factor, and leukemia inhibitory factor.

5. The method of claim 1, wherein the corneal limbal tissue is cultured until the corneal limbal cells become confluent.

6. The method of claim 1, wherein the corneal limbal cells are sorted using magnetic-affinity cell sorting (MACS).

7. The method of claim 1, wherein the corneal limbal cells are sorted using fluorescence-activated cell sorting (FACS).

8. The method of claim 1, wherein the undifferentiated cell-specific surface marker selected for is SSEA-4.

9. The method of claim 1, further comprising culturing the isolated population of pluripotent ELSCs to produce an embryonic-like stem cell line.

10. The method of claim 9, wherein the pluripotent ELSCs are cultured in culture media supplemented with one or more soluble factors selected from the group consisting of dimethyl sulphoxide, recombinant human epidermal growth factor, insulin, sodium selenite, transferrin, basic fibroblast growth factor, and leukemia inhibitory factor.

11. The method of claim 1, wherein the isolated population of pluripotent ELSCs comprises at least about 70% ELSCs.

12. The method of claim 1, wherein the pluripotent ELSCs remain substantially undifferentiated after 100 passages in culture.

13. The method of claim 1, further comprising the step of differentiating the human ELSCs into endodermal lineage-committed cells.

14. The method of claim 1, further comprising the step of differentiating the human ELSCs into mesodermal lineage-committed cells.

15. The method of claim 1, further comprising the step of differentiating the human ELSCs into ectodermal lineage-committed cells.

16. The method of claim 1, wherein the pluripotent ELSCs express a cell surface cluster differentiation marker selected from the group consisting of CD73, CD105, CD31, CD54, and CD117.

* * * * *

SEQUENCE LISTING

```
<160> NUMBER OF SEQ ID NOS: 12

<210> SEQ ID NO 1
<211> LENGTH: 26
<212> TYPE: DNA
<213> ORGANISM: Homo sapiens

<400> SEQUENCE: 1
tgaaggtcgg agtcaacgga tttggt                                         26

<210> SEQ ID NO 2
<211> LENGTH: 24
<212> TYPE: DNA
<213> ORGANISM: Homo sapiens

<400> SEQUENCE: 2
catgtgggcc atgaggtcca ccac                                           24

<210> SEQ ID NO 3
<211> LENGTH: 25
```

```
<212> TYPE: DNA
<213> ORGANISM: Homo sapiens

<400> SEQUENCE: 3
cgrgaagctg gagaaggaga agctg                                      25

<210> SEQ ID NO 4
<211> LENGTH: 25
<212> TYPE: DNA
<213> ORGANISM: Homo sapiens

<400> SEQUENCE: 4
caagggccgc agcttacaca tgttc                                      25

<210> SEQ ID NO 5
<211> LENGTH: 25
<212> TYPE: DNA
<213> ORGANISM: Homo sapiens

<400> SEQUENCE: 5
cctcctccat ggatctgctt attca                                      25

<210> SEQ ID NO 6
<211> LENGTH: 26
<212> TYPE: DNA
<213> ORGANISM: Homo sapiens

<400> SEQUENCE: 6
caggtcttca cctgtttgta gctgag                                     26

<210> SEQ ID NO 7
<211> LENGTH: 23
<212> TYPE: DNA
<213> ORGANISM: Homo sapiens

<400> SEQUENCE: 7
gcgtacgcaa attaaagtcc aga                                        23

<210> SEQ ID NO 8
<211> LENGTH: 25
<212> TYPE: DNA
<213> ORGANISM: Homo sapiens

<400> SEQUENCE: 8
cagcatccta aacagctcgc agaat                                      25

<210> SEQ ID NO 9
<211> LENGTH: 21
<212> TYPE: DNA
<213> ORGANISM: Homo sapiens

<400> SEQUENCE: 9
ggaagaacta ccagaaacgc g                                          21

<210> SEQ ID NO 10
<211> LENGTH: 21
<212> TYPE: DNA
<213> ORGANISM: Homo sapiens

<400> SEQUENCE: 10
agatgatcag ccagaggaaa a                                          21

<210> SEQ ID NO 11
<211> LENGTH: 26
```

```
<212> TYPE: DNA
<213> ORGANISM: Homo sapiens

<400> SEQUENCE: 11
aagaggacaa gaaggactaa aaatat                                      26

<210> SEQ ID NO 12
<211> LENGTH: 25
<212> TYPE: DNA
<213> ORGANISM: Homo sapiens

<400> SEQUENCE: 12
gtagagatcc agcataaaga gaggt                                       25
```